United States Patent
Uetani et al.

(10) Patent No.: US 6,548,220 B2
(45) Date of Patent: Apr. 15, 2003

(54) CHEMICAL AMPLIFYING TYPE POSITIVE RESIST COMPOSITION AND SULFONIUM SALT

(75) Inventors: Yasunori Uetani, Toyonaka (JP); Kenji Oohashi, Yawata (JP); Akira Kamabuchi, Ashiya (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/886,386

(22) Filed: Jun. 22, 2001

(65) Prior Publication Data

US 2002/0015913 A1 Feb. 7, 2002

(30) Foreign Application Priority Data

Jun. 23, 2000 (JP) ........................................ 2000-189120

(51) Int. Cl.[7] .............................................. G03F 7/004
(52) U.S. Cl. .................... 430/270.1; 430/905; 430/914; 430/921
(58) Field of Search .............................. 430/270.1, 914, 430/921, 905

(56) References Cited

U.S. PATENT DOCUMENTS

| | | |
|---|---|---|
| 5,585,507 A | 12/1996 | Nakano et al. |
| 5,635,332 A | 6/1997 | Nakano et al. |
| 5,691,111 A | 11/1997 | Iwasa et al. |
| 5,756,850 A | 5/1998 | Iwasa et al. |
| 5,968,713 A | 10/1999 | Nozaki et al. |

FOREIGN PATENT DOCUMENTS

| | | | |
|---|---|---|---|
| DE | 10054550 | * | 5/2001 |
| EP | 0 789 278 A2 | | 8/1997 |
| EP | 0 982 628 A2 | | 1/2000 |
| EP | 1 041 442 A1 | | 4/2000 |

OTHER PUBLICATIONS

Iwasa et al., J. Photopolymer Sci. and Tech., vol. 13, No. 2 (2000) pp. 235–236.

Mukaiyama, Teruaki et al., "Syntheses and Reactions of 2–Ethylthio– or or 2–Phenylthio–2–cycloalkenones"; Bulletin of the Chemical Society of Japan, vol. 44, No. 11; 1971, pp. 3155–3158.

* cited by examiner

Primary Examiner—Rosemary Ashton
(74) Attorney, Agent, or Firm—Birch, Stewart, Kolasch & Birch, LLP

(57) ABSTRACT

A chemical amplifying type positive resist composition which provides a resist pattern having an exceedingly improved line edge roughness, and is excellent in various resist performances such as dry etching resistance, sensitivity and resolution; and comprises:

(A) an acid generator containing (a) a sulfonium salt represented by the following formula (I):

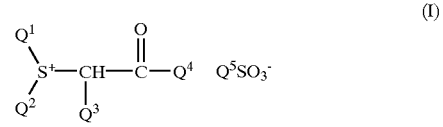

(I)

wherein $Q^1$ and $Q^2$ is alkyl or a cycloalkyl, or $Q^1$ and $Q^2$ form, together with a sulfur atom to which $Q^1$ and $Q^2$ are adjacent, an heteroalicyclic group; $Q^3$ represents a hydrogen atom, $Q^4$ represents alkyl or a cycloalkyl, or $Q^3$ and Q4 form, together with a CHC(O) group to which $Q^3$ and Q4 are adjacent, a 2-oxocycloalkyl group; and $Q^5SO_3^-$ represents an organosulfonate ion, and (b) at least one onium salt selected from a triphenylsulfonium salt represented by the following formula (IIa), and a diphenyliodonium salt represented by the following formula (IIb):

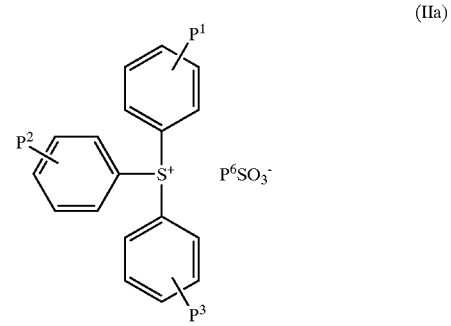

(IIa)

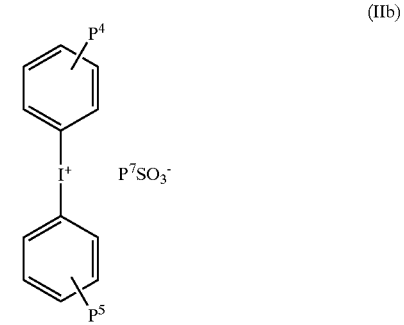

(IIb)

wherein $P^1$ to $P^5$ represent hydrogen, a hydroxyl group, alkyl, or alkoxy; and $P^6SO_3^-$ and $P^7SO_3^-$ each independently represent an organosulfonate ion; and (B) a resin which has a polymerization unit having a group instable against an acid, and is alkali-insoluble or -slightly soluble itself, but is converted to alkali-soluble by the action of an acid.

9 Claims, No Drawings

CHEMICAL AMPLIFYING TYPE POSITIVE RESIST COMPOSITION AND SULFONIUM SALT

FIELD OF THE INVENTION

The present invention relates to a chemical amplifying type positive resist composition for use in the fine processing of a semiconductor.

In general, a lithography process using a resist composition is adopted for the fine processing of a semiconductor. In lithography, the shorter the exposure light wavelength is, the more the resolution can be higher in principle, as shown by Rayleigh's formula for diffraction limited. Exposure light sources for lithography used for manufacturing a semiconductor, such as a g-line with a wavelength of 436 nm, an i-line with a wavelength of 365 nm, a KrF excimer laser with a wavelength of 248 nm, and an ArF excimer laser with a wavelength of 193 nm have been adopted. Thus, the wavelength thereof has been reduced year by year. A F2 excimer laser with a wavelength of 157 nm is regarded as being promising as the next-generation exposure light source. Thereafter, a soft X-ray (EUV) with a wavelength of not more than 13 nm is proposed as a light source.

Since a light source having a shorter wavelength than that of a g-line or an i-line, such as an excimer laser, has low illumination intensity, the sensitivity of a resist is required to be increased. For this reason, there is used a so-called chemical amplifying type resist containing a resin having a group utilizing the catalytic action of an acid which is generated through light exposure, and is cleaved by the acid.

However, with a chemical amplifying type resist composition known in the art, the line edge roughness, i.e., the smoothness of the pattern side wall is deteriorated due to the occurrence of a standing wave, or the like. As a result, there occurs a problem that the uniformity of the line width is deteriorated.

An object of the present invention is to provide a chemical amplifying type positive resist composition which comprises a resin component and an acid generator; is suitable for excimer laser lithography using an ArF excimer laser, a KrF excimer laser, or the like; is excellent in various resist performances such as sensitivity and resolution; and provides a particularly improved line edge roughness.

The present inventors have already found and proposed the following fact. Namely, by using at least one onium salt selected from triphenylsulfonium salt and diphenyliodonium salt, and a perfluoroalkylsulfonate salt of 2-oxosulfonium such as cyclohexylmethyl(2-oxosulufonium)perfluoroalkyl sulfonate in combination as an acid generator, the resolution is improved, and the profile on a basic substrate or a low reflectance substrate is also improved (Japanese Patent Application No.2000-060057). Thereafter, they have found that this combination system is also capable of improving the line edge roughness, and further conducted a study thereon. As a result, they have found that by using a specific sulfonium salt in place of the perfluoroalkylsulfonate salt of 2-oxosulfonium in the combination, it is possible to improve the line edge roughness. Thus, they have completed the present invention.

SUMMARY OF THE INVENTION

The present invention provides a practically excellent chemical amplifying type positive resist composition which comprises:

(A) an acid generator containing (a) a sulfonium salt represented by the following formula (I);

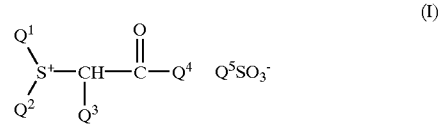

wherein $Q^1$ and $Q^2$ each independently represent a straight chain or branched alkyl group having from 1 to 6 carbon atoms or a cycloalkyl group having from 3 to 10 carbon atoms, or $Q^1$ and $Q^2$ form, together with a sulfur atom to which $Q^1$ and $Q^2$ are adjacent, heteroalicyclic group which may further contain an oxygen atom and a sulfur atom; $Q^3$ represents a hydrogen atom, $Q^4$ represents a straight chain or branched alkyl group having from 1 to 6 carbon atoms or a cycloalkyl group having from 3 to 10 carbon atoms, or $Q^3$ and $Q^4$ form, together with a CHC(O) group to which $Q^3$ and $Q^4$ are adjacent, a 2-oxocycloalkyl group; and $Q^5SO_3^-$ represents an organosulfonate ion, provided that when $Q^5$ represents a perfluoroalkyl group having from 1 to 8 carbon atoms, there is excluded the case where $Q^1$ represents a straight chain or branched alkyl group having from 1 to 6 carbon atoms, $Q^2$ represents a straight chain or branched alkyl group having from 1 to 6 carbon atoms, or a cycloalkyl group having from 3 to 10 carbon atoms, and $Q^3$ and $Q^4$ represent, together with their adjacent CHC(O) group, a 2-oxocycloalkyl group, and (b) at least one onium salt selected from a triphenylsulfonium salt represented by the following formula (IIa), and a diphenyliodonium salt represented by the following formula

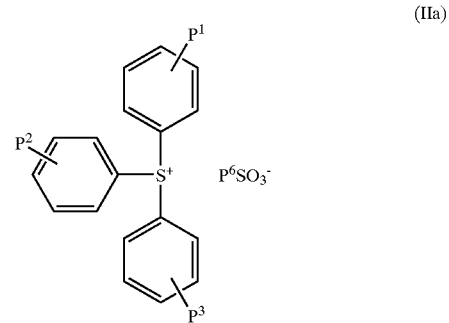

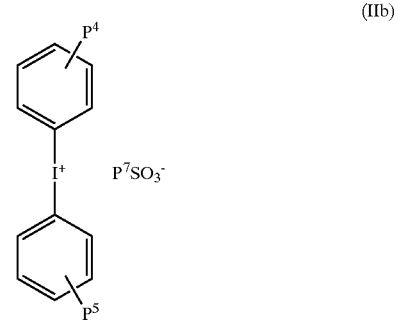

wherein $P^1$ to $P^5$ each independently represent hydrogen, a hydroxyl group, an alkyl group having from 1 to 6 carbon atoms, or an alkoxy group having from 1 to 6 carbon atoms; and $P^6SO_3^{31}$ and $P^7SO_3^-$ each independently represent an organosulfonate ion; and (B) a resin which has a polymerization unit having a group unstable against an acid, and is alkali-insoluble or -slightly soluble itself, but is converted to alkali-soluble by the action of an acid.

Further, the present invention also provides a sulfonium salt represented by the following formula (Ia):

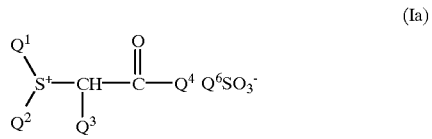

wherein $Q^6$ represents a perfluoroalkyl group having from 1 to 8 carbon atoms, an alkyl group having from 1 to 8 carbon atoms, an aromatic group having from 6 to 12 carbon atoms or a camphor group; when $Q^6$ represents a perfluoroalkyl group having from 1 to 8 carbon atoms, $Q^1$ and $Q^2$ each independently represent a straight chain or branched alkyl group having from 1 to 6 carbon atoms or a cycloalkyl group having from 3 to 10 carbon atoms, or $Q^1$ and $Q^2$ form, together with a sulfur atom to which $Q^1$ and $Q^2$ are adjacent, heteroalicyclic group which may further contain an oxygen atom and a sulfur atom, $Q^3$ represents a hydrogen atom, $Q^4$ represents a straight chain or branched alkyl group having from 1 to 6 carbon atoms or a cycloalkyl group having from 3 to 10 carbon atoms; when $Q^6$ represents an alkyl group having from 1 to 8 carbon atoms, an aromatic group having from 6 to 12 carbon atoms or a camphor group, $Q^1$ and $Q^2$ each independently represent a straight chain or branched alkyl group having from 1 to 6 carbon atoms or a cycloalkyl group having from 3 to 10 carbon atoms, or $Q^1$ and $Q^2$ form, together with a sulfur atom to which $Q^1$ and $Q^2$ are adjacent, a heteroalicyclic group which may further contain an oxygen atom and a sulfur atom, $Q^3$ represents a hydrogen atom, and $Q^4$ represents a straight chain or branched alkyl group having from 1 to 6 carbon atoms or a cycloalkyl group having from 3 to 10 carbon atoms, or $Q^3$ and $Q^4$ form, together with their adjacent CHC(O) group, a 2-oxocycloalkyl group.

DETAILED DESCRIPTION OF THE PREFERRED EMBODIMENTS

An acid generator to be used for a chemical amplifying type resist composition is decomposed to generate an acid by allowing a radiation such as light or an electron beam to act upon the substance itself or a resist composition containing the substance. In the composition of the present invention, as such an acid generator, a sulfonium salt represented by the formula (I), and at least one onium salt selected from a triphenylsulfonium salt represented by the formula (IIa), and a diphenyliodonium salt represented by the formula (IIb) are used in combination.

In the formula (I), $Q^1$ and $Q^2$ may be each independently an alkyl group having from 1 to 6 carbon atoms, or a cycloalkyl group having from 3 to 10 carbon atoms, and when they each have 3 or more carbon atoms, they may be strait-chain, or branched. Specific examples of an alkyl group and a cycloalkyl group include methyl group, ethyl group, propyl group, isopropyl group, butyl group, tert-butyl group, pentyl group, hexyl group, and cyclohexyl group. Further, examples of the heteroalicyclic group formed by $Q^1$ and $Q^2$ together with their adjacent sulfur atom include ethylene sulfide, trimethylene sulfide, tetrahydrothiophene, tetrahydrothiopyran, thioxane, dithiane, tetrahydrothiophen-3-one, and tetrahydrothiopyran-4-one. Among them, the heteroalicyclic group formed by $Q^1$ and $Q^2$ together with their adjacent sulfur atom, which may further contain an oxygen atom and a sulfur atom, is preferred in terms of thermal stability. If the thermal stability is good, it becomes possible to raise the bake temperature (PEB temperature). Generally speaking, the roughness is improved with an Increase in PEB temperature. Further, $Q^3$ may represent a hydrogen atom, $Q^4$ may represent a straight chain or branched alkyl group having from 1 to 6 carbon atoms or a cycloalkyl group having from 3 to 10 carbon atoms, or $Q^3$ and $Q^4$ may form, together with their adjacent CHC(O) group, a 2-oxocycloalkyl group. Specific examples of the alkyl group and cycloalkyl group as $Q^4$ include methyl group, ethyl group, propyl group, isopropyl group, butyl group, tert-butyl group, pentyl group, hexyl group, and cyclohexyl group. When $Q^3$ and $Q^4$ form, together with their adjacent CHC(O) group, a 2-oxocycloalkyl group, examples of such a 2-oxocycloalkyl group include 2-oxocyclohexyl group, 2-oxocyclopentyl group, camphor group, or the like.

In the formula (I), the $Q^5SO_3^-$ represents an organosulfonate ion. $Q^5$ may be an organic group having about from 1 to 12 carbon atoms, for example. Examples of the organic group as $Q^5$ include a perfluoroalkyl group having from 1 to 8 carbon atoms, an alkyl group having from 1 to 8 carbon atoms, an aromatic group having from 6 to 12 carbon atoms and a camphor group. Specific examples of the perfluoroalkyl group include trifluoromethyl group, perfluorobutyl group and perfluorooctyl group. Examples of the alkyl group having from 1 to 8 carbon atoms include methyl group, ethyl group, propyl group, isopropyl group, butyl group, pentyl group, hexyl group, cyclohexyl group, and octyl group. Examples of the aromatic group include phenyl group, tolyl group, xylyl group, mesityl group, and naphthyl group.

The sulfonium salt represented by the formula (I) can be produced in accordance with the method known in the art. For example, it can be produced in accordance with the following 10 reaction scheme by applying the method described in J. V. Crivello et al., "J. Polymer Science., Polymer Chemistry Edition", Vol.17, 2877–2892 (1979):

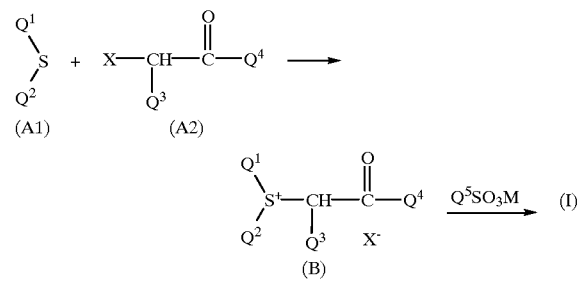

wherein $Q^1$, $Q^2$, $Q^3$, $Q^4$, and $Q^5$ are as defined above; X represents halogen such as bromine or iodine; and M represents a hydrogen atom, an alkali metal such as sodium or potassium, or silver.

Namely, β-halogenoketone corresponding to the formula (A2) is allowed to act upon a sulfide compound corresponding to the formula (A1) to form a sulfonium halide corresponding to the formula (B). Further, a sulfonic acid or a metal salt of a sulfonic acid corresponding to the formula $Q^5SO_3M$ is allowed to act thereon. Consequently, a sulfonium salt represented by the formula (I) can be obtained. These reactions are carried out in an appropriate solvent such as acetone, acetonitrile, or nitromethane. The sulfide compound of the formula (A1) is used in a molar ratio of preferably from 0.7 to 1.5, and more preferably from 0.8 to 1.1 relative to β-halogenoketone corresponding to the formula (A2). Whereas, the sulfonic acid or the metal salt of a sulfonic acid corresponding to the formula $Q^5SO_3M$ may be used in a molar ratio of from 0.7 to 1.2, and preferably from 0.8 to 1.0 relative to the sulfide compound of the formula (A1) used for the formation of the sulfonium halide of the formula (B). After completion of the reaction, the halogenated metal salt formed is removed by filtration or the like, and then post-treatments such as concentration and recrysatallization are performed. Consequently, a sulfonium salt of the formula (I) can be obtained.

Examples of the sulfonium salt represented by the formula (I) include:

dimethyl-(2-oxopropyl)sulfonium trifluoromethane sulfonate,
dimethyl-(2-oxobutyl)sulfonium trifluoromethane sulfonate,
dimethyl-(2-oxopentyl)sulfonium trifluoromethane sulfonate,
dimethyl-(2-oxohexyl)sulfonium trifluoromethane sulfonate,
dimethyl-(2-oxoheptyl)sulfonium trifluoromethane sulfonate,
dimethyl-(2-oxooctyl)sulfonium trifluoromethane sulfonate,
dimethyl-(3-methyl-2-oxobutyl)sulfonium trifluoromethane sulfonate,
3,3-dimethyl-2-oxobutyl dimethylsulfonium trifluoromethane sulfonate,
2-cyclohexyl-2-oxoethyl dimethylsulfonium trifluoromethane sulfonate,
2-cyclopentyl-2-oxoethyl dimethylsulfonium trifluoromethane sulfonate,
diethyl-(2-oxopropyl)sulfonium trifluoromethane sulfonate,
diethyl-(2-oxobutyl)sulfonium trifluoromethane sulfonate,
diethyl-(2-oxopentyl)sulfonium trifluoromethane sulfonate,
diethyl-(2-oxohexyl)sulfonium trifluoromethane sulfonate,
diethyl-(2-oxoheptyl)sulfonium trifluoromethane sulfonate,
diethyl-(2-oxooctyl)sulfonium trifluoromethane sulfonate,
diethyl-(3-methyl-2-oxobutyl)sulfonium trifluoromethane sulfonate,
3,3-dimethyl-2-oxobutyl diethylsulfonium trifluoromethane sulfonate,
2-cyclohexyl-2-oxoethyl diethylsulfonium trifluoromethane sulfonate,
2-cyclopentyl-2-oxoethyl diethylsulfonium trifluoromethane sulfonate,
dibutyl-(2-oxopropyl)sulfonium trifluoromethane sulfonate,
dibutyl-(2-oxobutyl)sulfonium trifluoromethane sulfonate,
dibutyl-(2-oxopentyl)sulfonium trifluoromethane sulfonate,
dibutyl-(2-oxohexyl)sulfonium trifluoromethane sulfonate,
dibutyl-(2-oxoheptyl)sulfonium trifluoromethane sulfonate,
dibutyl-(2-oxooctyl)sulfonium trifluoromethane sulfonate,
dibutyl-(3-methyl-2-oxobutyl)sulfonium trifluoromethane sulfonate,
dibutyl-(3,3-dimethyl-2-oxobutyl)sulfonium trifluoromethane sulfonate,
dibutyl-(2-cyclohexyl-2-oxoethyl)sulfonium trifluoromethane sulfonate,
dibutyl-(2-cyclopentyl-2-oxoethyl)sulfonium trifluoromethane sulfonate,
diisopropyl-(2-oxopropyl)sulfonium trifluoromethane sulfonate,
diisopropyl-(2-oxobutyl)sulfonium trifluoromethane sulfonate,
diisopropyl-(2-oxopentyl)sulfonium trifluoromethane sulfonate,
diisopropyl-(2-oxohexyl)sulfonium trifluoromethane sulfonate,
diisopropyl-(2-oxoheptyl)sulfonium trifluoromethane sulfonate,
diisopropyl-(2-oxooctyl)sulfonium trifluoromethane sulfonate,
diisopropyl- (3-methyl-2-oxobutyl)sulfonium trifluoromethane sulfonate,
3,3-dimethyl-2-oxobutyl diisopropylsulfonium trifluoromethane sulfonate,
2-cyclohexyl-2-oxoethyl diisopropylsulfonium trifluoromethane sulfonate,
2-cyclopentyl-2-oxoethyl diisopropylsulfonium trifluoromethane sulfonate,
tert-butyl methyl(2-oxopropyl)sulfonium trifluoromethane sulfonate,
tert-butyl methyl(2-oxobutyl)sulfonium trifluoromethane sulfonate,
tert-butyl methyl(2-oxopentyl)sulfonium trifluoromethane sulfonate,
tert-butyl methyl(2-oxohexyl)sulfonium trifluoromethane sulfonate,
tert-butyl methyl(2-oxoheptyl)sulfonium trifluoromethane sulfonate,
tert-butyl methyl(2-oxooctyl)sulfonium trifluoromethane sulfonate,
tert-butyl methyl(3-methyl-2-oxobutyl)sulfonium trifluoromethane sulfonate,
tert-butyl(3,3-dimethyl-2-oxobutyl)methylsulfonium trifluoromethane sulfonate,
tert-butyl(2-cyclohexyl-2-oxoethyl)methylsulfonium trifluoromethane sulfonate,
tert-butyl(2-cyclopentyl-2-oxoethyl)methylsulfonium trifluoromethane sulfonate,
cyclohexyl methyl(2-oxopropyl)sulfonium trifluoromethane sulfonate,
cyclohexyl methyl(2-oxabutyl)sulfonium trifluoromethane sulfonate,
cyclohexyl methyl(2-oxopentyl)sulfonium trifluoromethane sulfonate,
cyclohexyl methyl(2-oxohexyl)sulfonium trifluoromethane sulfonate,
cyclohexyl methyl(2-oxoheptyl)sulfonium trifluoromethane sulfonate,
cyclohexyl methyl(2-oxooctyl)sulfonium trifluoromethane sulfonate,
cyclohexyl methyl(3-methyl-2-oxobutyl)sulfonium trifluoromethane sulfonate,
cyclohexyl(3,3-dimethyl-2-oxobutyl)methylsulfonium trifluoromethane sulfonate,
cyclohexyl(2-cyclohexyl-2-oxoethyl)methylsulfonium trifluoromethane sulfonate,
cyclohexyl(2-cyclopentyl-2-oxoethyl)methylsulfonium trifluoromethane sulfonate,
2-oxopropyl thiacyclopentanium trifluoromethane sulfonate,
2-oxobutyl thiacyclopentanium trifluoromethane sulfonate,
2-oxopentyl thiacyclopentanium trifluoromethane sulfonate,
2-oxohexyl thiacyclopentanium trifluoromethane sulfonate,
2-oxoheptyl thiacyclopentanium trifluoromethane sulfonate,
2-oxooctyl thiacyclopentanium trifluoromethane sulfonate,
3-methyl-2-oxobutyl thiacyclopentanium trifluoromethane sulfonate,
3,3-dimethyl-2-oxobutyl thiacyclopentanium trifluoromethane sulfonate,
2-cyclohexyl-2-oxoethyl thiacyclopentanium trifluoromethane sulfonate,
2-cyclopentyl-2-oxoethyl thiacyclopentanium trifluoromethane sulfonate, 2-oxopropyl thiacyclohexanium trifluoromethane sulfonate,
2-oxobutyl thiacyclohexanium trifluoromethane sulfonate,
2-oxopentyl thiacyclohexanium trifluoromethane sulfonate,
2-oxohexyl thiacyclohexanium trifluoromethane sulfonate,
2-oxoheptyl thiacyclohexanium trifluoromethane sulfonate,
2-oxooctyl thiacyclohexanium trifluoromethane sulfonate,
3-methyl-2-oxobutyl thiacyclohexanium trifluoromethane sulfonate,
3,3-dimethyl-2-oxobutyl thiacyclohexanium trifluoromethane sulfonate,
2-cyclohexyl-2-oxoethyl thiacyclohexanium trifluoromethane sulfonate,
2-cyclopentyl-2-oxoethyl thiacyclohexanium trifluoromethane sulfonate,
2-oxopropyl(1,4-thioxanium)trifluoromethane sulfonate,
2-oxobutyl(1,4-thioxanium)trifluoromethane sulfonate,
2-oxopentyl(1,4-thioxanium)trifluoromethane sulfonate,
2-oxohexyl(1,4-thioxanium)trifluoromethane sulfonate,
2-oxoheptyl(1,4-thioxanium)trifluoromethane sulfonate,
2-oxooctyl(1,4-thioxanium)trifluoromethane sulfonate,
3-methyl-2-oxobutyl(1,4-thioxanium)trifluoromethane sulfonate,
3,3-dimethyl-2-oxobutyl(1,4-thioxanium)trifluoromethane sulfonate,
2-cyclohexyl-2-oxoethyl (1,4-thioxanium)trifluoromethane sulfonate,
2-cyclopentyl-2-oxoethyl (1,4-thioxanium)trifluoromethane sulfonate,
2-oxopropyl(4-oxothiacyclohexanium)trifluoromethane sulfonate,
2-oxobutyl(4-oxothiacyclohexanium)trifluoromethane sulfonate,
2-oxopentyl(4-oxothiacyclohexanium)trifluoromethane sulfonate,
2-oxohexyl(4-oxothiacyclohexanium)trifluoromethane sulfonate,
2-oxoheptyl(4-oxothiacyclohexanium)trifluoromethane sulfonate,
2-oxooctyl(4-oxothlacyclohexanium)trifluoromethane sulfonate,
3-methyl-2-oxobutyl(4-oxothiacyclohexanium) trifluoromethane sulfonate,
3,3-dimethyl-2-oxobutyl(4-oxothiacyclohexanium) trifluoromethane sulfonate,
2-cyclohexyl-2-oxoethyl(4-oxothiacyclohexanium) trifluoromethane sulfonate,
2-cyclopentyl-2-oxoethyl(4-oxothiacyclohexanium) trifluoromethane sulfonate,
2-oxopropyl(1,4-dithianium)trifluoromethane sulfonate,
2-oxobutyl(1,4-dithianium)trifluoromethane sulfonate,
2-oxopentyl(1,4-dithianium)trifluoromethane sulfonate,
2-oxohexyl(1,4-dithianium)trifluoromethane sulfonate,
2-oxoheptyl(1,4-dithianium)trifluoromethane sulfonate,
2-oxooctyl(1,4-dithianium)trifluoromethane sulfonate,
3-methyl-2-oxobutyl(1,4-dithianium)trifluoromethane sulfonate,
3,3-dimethyl-2-oxobutyl(1,4-dithianium)trifluoromethane sulfonate,
2-cyclohexyl-2-oxoethyl(1,4-dithianium)trifluoromethane sulfonate,
2-cyclopentyl-2-oxoethyl(1,4-dithianium)trifluoromethane sulfonate,
2-oxocyclohexyl thiacyclopentanium trifluoromethane sulfonate,
dimethyl-(2-oxopropyl)sulfonium perfluorobutane sulfonate,
dimethyl-(2-oxobutyl)sulfonium perfluorobutane sulfonate,
dimethyl-(2-oxopentyl)sulfonium perfluorobutane sulfonate,
dimethyl-(2-oxohexyl)sulfonium perfluorobutane sulfonate,
dimethyl-(2-oxoheptyl)sulfonium perfluorobutane sulfonate,
dimethyl-(2-oxooctyl)sulfonium perfluorobutane sulfonate,
dimethyl-(3-methyl-2-oxobutyl)sulfonium perfluorobutane sulfonate,
3,3-dimethyl-2-oxobutyl dimethylsulfonium perfluorobutane sulfonate,
2-cyclohexyl-2-oxoethyl dimethylsulfonium perfluorobutane sulfonate,
2cyclopentyl- 2 -oxoethyl dimethylsulfonium perfluorobutane sulfonate,
diethyl-(2-oxopropyl)sulfonium perfluorobutane sulfonate,
diethyl-(2-oxobutyl)sulfonium perfluorobutane sulfonate,
diethyl-(2-oxopentyl)sulfonium perfluorobutane sulfonate,
diethyl-(2-oxohexyl)sulfonium perfluorobutane sulfonate,
diethyl-(2-oxoheptyl)sulfonium perfluorobutane sulfonate,
diethyl-(2-oxooctyl)sulfonium perfluorobutane sulfonate,
diethyl-3-methyl-2-oxobutyl)sulfonium perfluorobutane sulfonate,
3,3-dimethyl-2-oxobutyl diethylsulfonium perfluorobutane sulfonate,
2-cyclohexyl-2-oxoethyl diethylsulfonium perfluorobutane sulfonate,
2-cyclopentyl-2-oxoethyl diethylsulfonium perfluorobutane sulfonate,
dibutyl-(2-oxopropyl)sulfonium perfluorobutane sulfonate,
dibutyl-(2-oxobutyl)sulfonium perfluorobutane sulfonate,
dibutyl-(2-oxopentyl)sulfonium perfluorobutane sulfonate,
dibutyl-(2-oxohexyl)sulfonium perfluorobutane sulfonate,
dibutyl-(2-oxoheptyl)sulfonium perfluorobutane sulfonate,
dibutyl-(2-oxooctyl)sulfonium perfluorobutane sulfonate,
dibutyl-(3-methyl-2-oxobutyl)sulfonium perfluorobutane sulfonate, dibutyl-(3,3-dimethyl-2-oxobutyl)sulfonium perfluorobutane sulfonate,
dibutyl-(2-cyclohexyl-2-oxoethyl)sulfonium perfluorobutane sulfonate,
dibutyl-(2-cyclopentyl-2-oxoethyl)sulfonium perfluorobutane sulfonate,
diisopropyl-(2-oxopropyl)sulfonium perfluorobutane sulfonate, diisopropyl-(2-oxobutyl)sulfonium perfluorobutane sulfonate,
diisopropyl-(2-oxopentyl)sulfonium perfluorobutane sulfonate, diisopropyl-(2-oxohexyl)sulfonium perfluorobutane sulfonate,
diisopropyl-(2-oxoheptyl)sulfonium perfluorobutane sulfonate, diisopropyl-(2-oxooctyl)sulfonium perfluorobutane sulfonate,
diisopropyl-(3-methyl-2-oxobutyl)sulfonium perfluorobutane sulfonate,
3,3-dimethyl-2-oxobutyl diisopropylsulfonium perfluorobutane sulfonate,
2-cyclohexyl-2-oxoethyl diisopropylsulfonium perfluorobutane sulfonate,
2-cyclopentyl-2-oxoethyl diisopropylsulfonium perfluorobutane sulfonate,
tert-butyl methyl(2-oxopropyl)sulfonium perfluorobutane sulfonate,
tert-butyl methyl(2-oxobutyl)sulfonium perfluorobutane sulfonate,
tert-butyl methyl(2-oxopentyl)sulfonium perfluorobutane sulfonate,
tert-butyl methyl(2-oxohexyl)sulfonium perfluorobutane sulfonate,
tert-butyl methyl(2-oxoheptyl)sulfonium perfluorobutane sulfonate, tert-butyl methyl(2-oxooctyl)sulfonium perfluorobutane sulfonate,
tert-butyl methyl(3-methyl-2-oxobutyl)sulfonium perfluorobutane sulfonate,
tert-butyl(3,3-dimethyl-2-oxobutyl)methylsulfonium perfluorobutane sulfonate,
tert-butyl(2-cyclohexyl-2-oxoethyl)methylsulfonium perfluorobutane sulfonate,
tert-butyl(2-cyclopentyl-2-oxoethyl)methylsulfonium perfluorobutane sulfonate,
cyclohexyl methyl(2-oxopropyl)sulfonium perfluorobutane sulfonate, cyclohexyl methyl(2-oxobutyl)sulfonium perfluorobutane sulfonate, cyclohexyl methyl(2-oxopentyl)sulfonium perfluorobutane sulfonate, cyclohexyl methyl(2-oxohexyl)sulfonium perfluorobutane sulfonate,
cyclohexyl methyl(2-oxoheptyl)sulfonium perfluorobutane sulfonate,
cyclohexyl methyl(2-oxooctyl)sulfonium perfluorobutane sulfonate,
cyclohexyl methyl(3-methyl-2-oxobutyl)sulfonium perfluorobutane sulfonate,
cyclohexyl(3,3-dimethyl-2-oxobutyl)methylsulfonium perfluorobutane sulfonate,
cyclohexyl(2-cyclohexyl-2-oxoethyl)methylsulfonium perfluorobutane sulfonate,
cyclohexyl(2-cyclopentyl-2-oxoethyl)methylsulfonium perfluorobutane sulfonate,
2-oxopropyl thiacyclopentanium perfluorobutane sulfonate
2-oxobutyl thiacyclopentanium perfluorobutane sulfonate,
2-oxopentyl thiacyclopentanium perfluorobutane sulfonate,
2-oxohexyl thiacyclopentanium perfluorobutane sulfonate,
2-oxoheptyl thiacyclopentanium perfluorobutane sulfonate,
2-oxooctyl thiacyclopentanium perfluorobutane sulfonate,
3-methyl-2-oxobutyl thiacyclopentanium perfluorobutane sulfonate,
3,3-dimethyl-2-oxobutyl thiacyclopentanium perfluorobutane sulfonate,
2-cyclohexyl-2-oxoethyl thiacyclopentanium perfluorobutane sulfonate,
2-cyclopentyl-2-oxoethyl thiacyclopentanium perfluorobutane sulfonate,
2-oxopropyl thiacyclohexanium perfluorobutane sulfonate,
2-oxobutyl thiacyclohexanium perfluorobutane sulfonate,
2-oxopentyl thiacyclohexanium perfluorobutane sulfonate,
2-oxohexyl thiacyclohexanium perfluorobutane sulfonate,
2-oxoheptyl thiacyclohexanium perfluorobutane sulfonate,
2-oxooctyl thiacyclohexanium perfluorobutane sulfonate,
3-methyl-2-oxobutyl thiacyclohexanium perfluorobutane sulfonate,
3,3-dimethyl-2-oxobutyl thiacyclohexanium perfluorobutane sulfonate,
2-cyclohexyl-2-oxoethyl thiacyclohexanium perfluorobutane sulfonate,
2-cyclopentyl-2-oxoethyl thiacyclohexanium perfluorobutane sulfonate,
2-oxopropyl(1,4-thioxanium)perfluorobutane sulfonate,
2-oxobutyl(1,4-thioxanium)perfluorobutane sulfonate,
2-oxopentyl(1,4-thioxanium)perfluorobutane sulfonate,
2-oxohexyl(1,4-thioxanium)perfluorobutane sulfonate,
2-oxoheptyl(1,4-thioxanium)perfluorobutane sulfonate,
2-oxooctyl(1,4-thioxanium)perfluorobutane sulfonate,
3-methyl-2-oxobutyl(1,4-thioxanium)perfluorobutane sulfonate,
3,3-dimethyl-2-oxobutyl(1,4-thioxanium)perfluorobutane sulfonate,
2-cyclohexyl-2-oxoethyl(1,4-thioxanium)perfluorobutane sulfonate,
2-cyclopentyl-2-oxoethyl(1,4-thioxanium)perfluorobutane sulfonate,
2-oxopropyl(4-oxothiacyclohexanium)perfluorobutane sulfonate,
2-oxobutyl(4-oxothiacyclohexanium)perfluorobutane sulfonate,
2-oxopentyl(4-oxothiacyclohexanium)perfluorobutane sulfonate,
2-oxohexyl(4-oxothiacyclohexanium)perfluorobutane sulfonate,
2-oxoheptyl(4-oxothiacyclohexanium)perfluorobutane sulfonate,
2-oxooctyl(4-oxothiacyclohexanium)perfluorobutane sulfonate,
3-methyl-2-oxobutyl(4-oxothiacyclohexanium) perfluorobutane sulfonate,
3,3-dimethyl-2-oxobutyl(4-oxothiacyclohexanium) perfluorobutane sulfonate,
2-cyclohexyl-2-oxoethyl(4-oxothiacyclohexanium) perfluorobutane sulfonate,
2-cyclopentyl-2-oxoethyl(4-oxothiacyclohexanium) perfluorobutane sulfonate,
2-oxopropyl(1,4-dithianium)perfluorobutane sulfonate,
2-oxobutyl(1,4-dithianium)perfluorobutane sulfonate,
2-oxopentyl(1,4-dithianium)perfluorobutane sulfonate,
2-oxohexyl(1,4-dithianium)perfluorobutane sulfonate,
2-oxoheptyl(1,4-dithianium)perfluorobutane sulfonate,
2-oxooctyl(1,4-dithianium)perfluorobutane sulfonate,
3-methyl-2-oxobutyl(1,4-dithianium)perfluorobutane sulfonate,
3,3-dimethyl-2-oxobutyl(1,4-dithianium)perfluorobutane sulfonate,
2-cyclohexyl-2-oxoethyl(1,4-dithianium)perfluorobutane sulfonate,
2-cyclopentyl-2-oxoethyl(1,4-dithianium)perfluorobutane sulfonate,
2-oxocyclohexyl thiacyclopentanium perfluorobutane sulfonate,
dimethyl-(2-oxopropyl)sulfonium perfluorooctane sulfonate,
dimethyl-(2-oxobutyl)sulfonium perfluorooctane sulfonate,
dimethyl-(2-oxopentyl)sulfonium perfluorooctane sulfonate,
dimethyl-(2-oxohexyl)sulfonium perfluorooctane sulfonate,
dimethyl-(2-oxoheptyl)sulfonium perfluorooctane sulfonate,
dimethyl-(2-oxooctyl)sulfonium perfluorooctane sulfonate,
dimethyl-(3-methyl-2-oxobutyl)sulfonium perfluorooctane sulfonate,
3,3-dimethyl-2-oxobutyl dimethylsulfonium perfluorooctane sulfonate,
2-cyclohexyl-2-oxoethyl dimethylsulfonium perfluorooctane sulfonate,
2-cyclopentyl-2-oxoethyl dimethylsulfonium perfluorooctane sulfonate,
diethyl-(2-oxopropyl)sulfonium perfluorooctane sulfonate,
diethyl-(2-oxobutyl)sulfonium perfluorooctane sulfonate,
diethyl-(2-oxopentyl)sulfonium perfluorooctane sulfonate,
diethyl-(2-oxohexyl)sulfonium perfluorooctane sulfonate,
diethyl-(2-oxoheptyl)sulfonium perfluorooctane sulfonate,
diethyl-(2-oxooctyl)sulfonium perfluorooctane sulfonate,
diethyl-(3-methyl-2-oxobutyl)sulfonium perfluorooctane sulfonate,
3,3-dimethyl-2-oxobutyl diethylsulfonium perfluorooctane sulfonate,
2-cyclohexyl-2-oxoethyl diethylsulfonium perfluorooctane sulfonate, 2-cyclopentyl-2-oxoethyl diethylsulfonium perfluorooctane sulfonate,
dibutyl-(2-oxopropyl)sulfonium perfluorooctane sulfonate,
dibutyl-(2-oxobutyl)sulfonium perfluorooctane sulfonate,
dibutyl-(2-oxopentyl)sulfonium perfluorooctane sulfonate,
dibutyl-(2-oxohexyl)sulfonium perfluorooctane sulfonate,
dibutyl-(2-oxoheptyl)sulfonium perfluorooctane sulfonate,
dibutyl-(2-oxooctyl)sulfonium perfluorooctane sulfonate,
dibutyl-(3-methyl-2-oxobutyl)sulfonium perfluorooctane sulfonate,
dibutyl-(3,3-dimethyl-2-oxobutyl)sulfonium perfluorooctane sulfonate,
dibutyl-(2-cyclohexyl-2-oxoethyl)sulfonium perfluorooctane sulfonate,
dibutyl-(2-cyclopentyl-2-oxoethyl)sulfonium perfluorooctane sulfonate,
diisopropyl-(2-oxopropyl)sulfonium perfluorooctane sulfonate, diisopropyl-(2-oxobutyl)sulfonium perfluorooctane sulfonate,
diisopropyl-(2-oxopentyl)sulfonium perfluorooctane sulfonate, diisopropyl-(2-oxohexyl)sulfonium perfluorooctane sulfonate,
diisopropyl-(2-oxopentyl)sulfonium perfluorooctane sulfonate, diisopropyl-(2-oxooctyl)sulfonium perfluorooctane sulfonate,
diisopropyl-(3-methyl-2-oxobutyl)sulfonium perfluorooctane sulfonate,
3,3-dimethyl-2-oxobutyl diisopropylsulfonium perfluorooctane sulfonate,
2-cyclohexyl-2-oxoethyl diisopropylsulfonium perfluorooctane sulfonate,
2-cyclopentyl-2-oxoethyl diisopropylsulfonium perfluorooctane sulfonate,
tert-butyl methyl(2-oxopropyl)sulfonium perfluorooctane sulfonate,
tert-butyl methyl(2-oxobutyl)sulfonium perfluorooctane sulfonate,
tert-butyl methyl(2-oxopentyl)sulfonium perfluorooctane sulfonate,
tert-butyl methyl(2-oxohexyl)sulfonium perfluorooctane sulfonate,
tert-butyl methyl(2-oxoheptyl)sulfonium perfluorooctane sulfonate,
tert-butyl methyl(2-oxooctyl)sulfonium perfluorooctane sulfonate,
tert-butyl methyl(3-methyl-2-oxobutyl)sulfonium perfluorooctane sulfonate,
tert-butyl(3,3-dimethyl-2-oxobutyl)methylsulfonium perfluorooctane sulfonate,
tert-butyl(2-cyclohexyl-2-oxoethyl)methylsulfonium perfluorooctane sulfonate,
tert-butyl(2-cyclopentyl-2-oxoethyl)methylsulfonium perfluorooctane sulfonate,
cyclohexyl methyl(2-oxopropyl)sulfonium perfluorooctane sulfonate, cyclohexyl methyl(2-oxobutyl)sulfonium perfluorooctane sulfonate, cyclohexyl methyl(2-oxopentyl)sulfonium perfluorooctane sulfonate,
cyclohexyl methyl(2-oxohexyl)sulfonium perfluorooctane sulfonate,
cyclohexyl methyl(2-oxoheptyl)sulfonium perfluorooctane sulfonate,
cyclohexyl methyl(2-oxooctyl)sulfonium perfluorooctane sulfonate,
cyclohexyl methyl(3-methyl-2-oxobutyl)sulfonium perfluorooctane sulfonate,
cyclohexyl(3,3-dimethyl-2-oxobutyl)sulfonium perfluorooctane sulfonate,
cyclohexyl(2-cyclohexyl-2-oxoethyl)methylsulfonium perfluorooctane sulfonate,
cyclohexyl(2-cyclopentyl-2-oxoethyl)methylsulfonium perfluorooctane sulfonate,
2-oxopropyl thiacyclopentanium perfluorooctane methylsulfonate,
2-oxobutyl thiacyclopentanium perfluorooctane sulfonate,
2-oxopentyl thiacyclopentanium perfluorooctane sulfonate,
2-oxohexyl thiacyclopentanium perfluorooctane sulfonate,
2-oxoheptyl thiacyclopentanium perfluorooctane sulfonate,
2-oxooctyl thiacyclopentanium perfluorooctane sulfonate,
3-methyl-2-oxobutyl thiacyclopentanium perfluorooctane sulfonate,
3, 3-dimethyl-2-oxobutyl thiacyclopentanium perfluorooctane sulfonate,
2-cyclohexyl-2-oxoethyl thiacyclopentanium perfluorooctane sulfonate,
2-cyclopentyl-2-oxoethyl thiacyclopentanium perfluorooctane sulfonate,
2-oxopropyl thiacyclohexanium perfluorooctane sulfonate,
2-oxobutyl thiacyclohexanium perfluorooctane sulfonate,
2-oxopentyl thiacyclohexanium perfluorooctane sulfonate,
2-oxohexyl thiacyclohexanium perfluorooctane sulfonate,
2-oxoheptyl thiacyclohexanium perfluorooctane sulfonate,
2-oxooctyl thiacyclohexanium perfluorooctane sulfonate,
3-methyl-2-oxobutyl thiacyclohexanium perfluorooctane sulfonate,
3,3-dimethyl-2-oxobutyl thiacyclohexanium perfluorooctane sulfonate,
2-cyclohexyl-2-oxoethyl thiacyclohexanium perfluorooctane sulfonate,
2-cyclopentyl-2-oxoethyl thiacyclohexanium perfluorooctane sulfonate,
2-oxopropyl(1,4-thioxanium)perfluorooctane sulfonate,
2-oxobutyl(1,4-thioxanium)perfluorooctane sulfonate,
2-oxopentyl(1,4-thioxanium)perfluorooctane sulfonate,
2-oxohexyl(1,4-thioxanium)perfluorooctane sulfonate,
2-oxoheptyl(1,4-thioxanium)perfluorooctane sulfonate,
2-oxooctyl(1,4-thioxanium)perfluorooctane sulfonate,
3-methyl-2-oxobutyl(1,4-thioxanium)perfluorooctane sulfonate,
3,3-dimethyl-2-oxobutyl(1,4-thioxanium)perfluorooctane sulfonate,
2-cyclohexyl-2-oxoethyl(1,4-thioxanium)perfluorooctane sulfonate,
2-cyclopentyl-2-oxoethyl(1,4-thioxanium)perfluorooctane sulfonate,
2-oxopropyl(4-oxothiacyclohexanium)perfluorooctane sulfonate,
2-oxobutyl(4-oxothiacyclohexanium)perfluorooctane sulfonate,
2-oxopentyl(4-oxothiacyclohexanium)perfluorooctane sulfonate,
2-oxohexyl(4-oxothiacyclohexanium)perfluorooctane sulfonate,
2-oxoheptyl(4-oxothiacyclohexanium)perfluorooctane sulfonate,
2-oxooctyl(4-oxothiacyclohexanium)perfluorooctane sulfonate,
3-methyl-2-oxobutyl(4-oxothiacyclohexanium) perfluorooctane sulfonate,
3,3-dimethyl-2-oxobutyl(4-oxothiacyclohexanium) perfluorooctane sulfonate,
2-cyclohexyl-2-oxoethyl(4-oxothiacyclohexanium) perfluorooctane sulfonate,
2-cyclopentyl-2-oxoethyl(4-oxothiacyclohexanium) perfluorooctane sulfonate, 2-oxopropyl(1,4-dithianium)perfluorooctane sulfonate,
2-oxobutyl(1,4-dithianium)perfluorooctane sulfonate,
2-oxopentyl(1,4-dithianium)perfluorooctane sulfonate,
2-oxohexyl(1,4-dithianium)perfluorooctane sulfonate,
2-oxoheptyl(1,4-dithianium)perfluorooctane sulfonate,
2-oxooctyl(1,4-dithianium)perfluorooctane sulfonate,
3-methyl-2-oxobutyl(1,4-dithianium)perfluorooctane sulfonate,
3,3-dimethyl-2-oxobutyl(1,4-dithianium)perfluorooctane sulfonate,
2-cyclohexyl-2-oxoethyl(1,4-dithianium)perfluorooctane sulfonate,
2-cyclopentyl-2-oxoethyl(1,4-dithianium)perfluorooctane sulfonate,
2-oxocyclohexyl thiacyclopentanium perfluorooctane sulfonate,
dimethyl-(2-oxopropyl)sulfonium butane sulfonate,
dimethyl-(2-oxobutyl)sulfonium butane sulfonate,
dimethyl-(2-oxopentyl)sulfonium butane sulfonate,
dimethyl-(2-oxohexyl)sulfonium butane sulfonate,
dimethyl-(2-oxoheptyl)sulfonium butane sulfonate,
dimethyl-(2-oxooctyl)sulfonium butane sulfonate,
dimethyl-(3-methyl-2-oxobutyl)sulfonium butane sulfonate,
3,3-dimethyl-2-oxobutyl dimethylsulfonium butane sulfonate,
2-cyclohexyl-2-oxoethyl dimethylsulfonium butane sulfonate,
2-cyclopentyl-2-oxoethyl dimethylsulfonium butane sulfonate,
diethyl-(2-oxopropyl)sulfonium butane sulfonate,
diethyl-(2-oxobutyl)sulfonium butane sulfonate,
diethyl-(2-oxopentyl)sulfonium butane sulfonate,
diethyl-(2-oxohexyl)sulfonium butane sulfonate,
diethyl-(2-oxoheptyl)sulfonium butane sulfonate,
diethyl-(2-oxooctyl)sulfonium butane sulfonate,
diethyl-(3-methyl-2-oxobutyl)sulfonium butane sulfonate,
3,3-dimethyl-2-oxobutyl diethylsulfonium butane sulfonate,
2-cyclohexyl-2-oxoethyl diethylsulfonium butane sulfonate,
2-cyclopentyl-2-oxoethyl diethylsulfonium butane sulfonate,
dibutyl-(2-oxopropyl)sulfonium butane sulfonate,
dibutyl-(2-oxobutyl)sulfonium butane sulfonate,
dibutyl-(2-oxopentyl)sulfonium butane sulfonate,
dibutyl-(2-oxohexyl)sulfonium butane sulfonate,
dibutyl-(2-oxoheptyl)sulfonium butane sulfonate,
dibutyl-(2-oxooctyl)sulfonium butane sulfonate,
dibutyl-(3-methyl-2-oxobutyl)sulfonium butane sulfonate,
dibutyl-(3,3-dimethyl-2-oxobutyl)sulfonium butane sulfonate,
dibutyl-(2-cyclohexyl-2-oxoethyl)sulfonium butane sulfonate,
dibutyl-(2-cyclopentyl-2-oxoethyl)sulfonium butane sulfonate,
diisopropyl-(2-oxopropyl)sulfonium butane sulfonate,
diisopropyl-(2-oxobutyl)sulfonium butane sulfonate,
diisopropyl-(2-oxopentyl)sulfonium butane sulfonate,
diisopropyl-(2 - oxohexyl)sulfonium butane sulfonate,
diisopropyl-(2-oxoheptyl)sulfonium butane sulfonate,
diisopropyl-(2-oxooctyl)sulfonium butane sulfonate,
diisopropyl-(3-methyl-2-oxobutyl)sulfonium butane sulfonate,
3,3-dimethyl-2-oxobutyl diisopropylsulfonium butane sulfonate,
2-cyclohexyl-2-oxoethyl diisopropylsulfonium butane sulfonate,
2-cyclopentyl-2-oxoethyl diisopropylsulfonium butane sulfonate,
tert-butyl methyl(2-oxopropyl)sulfonium butane sulfonate,
tert-butyl methyl(2-oxobutyl)sulfonium butane sulfonate,
tert-butyl methyl(2-oxopentyl)sulfonium butane sulfonate,
tert-butyl methyl(2-oxohexyl)sulfonium butane sulfonate,
tert-butyl methyl(2-oxoheptyl)sulfonium butane sulfonate,
tert-butyl methyl(2-oxooctyl)sulfonium butane sulfonate,
tert-butyl methyl(3-methyl-2-oxobutyl)sulfonium butane sulfonate,
tert-butyl(3,3-dimethyl-2-oxobutyl)methylsulfonium butane sulfonate,
tert-butyl(2 -cyclohexyl-2-oxoethyl)methylsulfonium butane sulfonate,
tert-butyl(2-cyclopentyl-2-oxoethyl)methylsulfonium butane sulfonate,
cyclohexyl methyl(2-oxopropyl)sulfonium butane sulfonate,
cyclohexyl methyl(2-oxobutyl)sulfonium butane sulfonate,
cyclohexyl methyl(2-oxopentyl)sulfonium butane sulfonate,
cyclohexyl methyl(2-oxohexyl)sulfonium butane sulfonate,
cyclohexyl methyl(2-oxoheptyl)sulfonium butane sulfonate,
cyclohexyl methyl(2-oxooctyl)sulfonium butane sulfonate,
cyclohexyl methyl(3-methyl-2-oxobutyl)sulfonium butane sulfonate,
cyclohexyl(3,3-dimethyl-2-oxobutyl)methylsulfonium butane sulfonate,
cyclohexyl(2-cyclohexyl-2-oxoethyl)methylsulfonium butane sulfonate,
cyclohexyl(2-cyclopentyl-2-oxoethyl)methylsulfonium butane sulfonate,
2-oxopropyl thiacyclopentanium butane sulfonate,
2-oxobutyl thiacyclopentanium butane sulfonate,
2-oxopentyl thiacyclopentanium butane sulfonate,
2-oxohexyl thiacyclopentanium butane sulfonate,
2-oxoheptyl thiacyclopentanium butane sulfonate,
2-oxooctyl thiacyclopentanium butane sulfonate,
3-methyl-2-oxobutyl thiacyclopentanium butane sulfonate,
3, 3-dimethyl-2-oxobutyl thiacyclopentanium butane sulfonate,
2-cyclohexyl-2-oxoethyl thiacyclopentanium butane sulfonate,
2-cyclopentyl-2-oxoethyl thiacyclopentanium butane sulfonate,
2-oxopropyl thiacyclohexanium butane sulfonate,
2-oxobutyl thiacyclohexanium butane sulfonate,
2-oxopentyl thiacyclohexanium butane sulfonate,
2-oxohexyl thiacyclohexanium butane sulfonate,
2-oxoheptyl thiacyclohexanium butane sulfonate,
2-oxooctyl thiacyclohexanium butane sulfonate,
3-methyl-2-oxobutyl thiacyclohexanium butane sulfonate,
3,3-dimethyl-2-oxobutyl thiacyclohexanium butane sulfonate,
2-cyclohexyl-2-oxoethyl thiacyclohexanium butane sulfonate,
2-cyclopentyl-2-oxoethyl thiacyclohexanium butane sulfonate,
2-oxopropyl(1,4-thioxanium)butane sulfonate,
2-oxobutyl(1,4-thioxanium)butane sulfonate,
2-oxopentyl(1,4-thioxanium)butane sulfonate,
2-oxohexyl(1,4-thioxanium)butane sulfonate,
2-oxoheptyl(1,4-thioxanium)butane sulfonate,
2-oxooctyl(1,4-thioxanium)butane sulfonate,
3-methyl-2-oxobutyl(1,4-thioxanium)butane sulfonate,
3,3-dimethyl-2-oxobutyl(1,4-thioxanium)butane sulfonate,
2-cyclohexyl-2-oxoethyl(1,4-thioxanium)butane sulfonate,
2-cyclopentyl-2-oxoethyl(1,4-thioxanium)butane sulfonate,
2-oxopropyl(4-oxothiacyclohexanium)butane sulfonate,
2-oxobutyl(4-oxothiacyclohexanium)butane sulfonate, 2-oxopentyl(4-oxothiacyclohexanium)butane sulfonate,
2-oxohexyl(4-oxothiacyclohexanium)butane sulfonate,
2-oxoheptyl(4-oxothiacyclohexanium)butane sulfonate,
2-oxooctyl(4-oxothiacyclohexanium)butane sulfonate,
3-methyl-2-oxobutyl(4-oxothiacyclohexanium )butane sulfonate,
3,3-dimethyl-2-oxobutyl(4-oxothiacyclohexanium)butane sulfonate,
2-cyclohexyl-2-oxoethyl(4-oxothiacyclohexanium)butane sulfonate,
2-cyclopentyl-2-oxoethyl(4-oxothiacyclohexanium)butane sulfonate,
2-oxopropyl(1,4-dithianium)butane sulfonate,
2-oxobutyl(1,4-dithianium)butane sulfonate,
2-oxopentyl(1,4-dithianium)butane sulfonate,
2-oxohexyl(1,4-dithianium)butane sulfonate,
2-oxoheptyl(1,4-dithianium)butane sulfonate,
2-oxooctyl(1,4-dithianium)butane sulfonate,
3-methyl-2-oxobutyl(1,4-dithianium)butane sulfonate,
3,3-dimethyl-2-oxobutyl(1,4-dithianium)butane sulfonate,
2-cyclohexyl-2-oxoethyl(1,4-dithianium)butane sulfonate,
2-cyclopentyl-2-oxoethyl(1,4-dithianium)butane sulfonate,
2-oxocyclohexyl thiacyclopentanium butane sulfonate,
dimethyl-(2-oxopropyl)sulfonium p-toluene sulfonate,
dimethyl-(2-oxobutyl)sulfonium p-toluene sulfonate,
dimethyl-(2-oxopentyl)sulfonium p-toluene sulfonate,
dimethyl-(2-oxohexyl)sulfonium p-toluene sulfonate,
dimethyl-(2-oxoheptyl)sulfonium p-toluene sulfonate,
dimethyl-(2-oxohexyl)sulfonium p-toluene sulfonate,
dimethyl-(3-methyl-2-oxobutyl)sulfonium p-toluene sulfonate,
3,3-dimethyl-2-oxobutyl dimethylsulfonium p-toluene sulfonate,
2-cyclohexyl-2-oxoethyl dimethylsulfonium p-toluene sulfonate,
2-cyclopentyl-2-oxoethyl dimethylsulfonium p-toluene sulfonate,
diethyl-(2-oxopropyl)sulfonium p-toluene sulfonate,
diethyl-(2-oxobutyl)sulfonium p-toluene sulfonate,
diethyl-(2-oxopentyl)sulfonium p-toluene sulfonate,
diethyl-(2-oxohexyl)sulfonium p-toluene sulfonate,
diethyl-(2-oxoheptyl)sulfonium p-toluene sulfonate,
diethyl-(2-oxooctyl)sulfonium p-toluene sulfonate,
diethyl-(3-methyl-2-oxobutyl)sulfonium p-toluene sulfonate,
3,3-dimethyl-2-oxobutyl diethylsulfonium p-toluene sulfonate,
2-cyclohexyl-2-oxoethyl diethylsulfonium p-toluene sulfonate,
2-cyclopentyl-2-oxoethyl diethylsulfonium p-toluene sulfonate,
dibutyl-(2-oxopropyl)sulfonium p-toluene sulfonate,
dibutyl-(2-oxobutyl)sulfonium p-toluene sulfonate,
dibutyl-(2-oxopentyl)sulfonium p-toluene sulfonate
dibutyl-(2-oxohexyl)sulfonium p-toluene sulfonate,
dibutyl-(2-oxoheptyl)sulfonium p-toluene sulfonate,
dibutyl-(2-oxooctyl)sulfonium p-toluene sulfonate,
dibutyl-(3-methyl-2-oxobutyl)sulfonium p-toluene sulfonate,
dibutyl-(3,3-dimethyl-2-oxobutyl)sulfonium p-toluene sulfonate,
dibutyl-(2-cyclohexyl-2-oxoethyl)sulfonium p-toluene sulfonate,
dibutyl-(2-cyclopentyl-2-oxoethyl)sulfonium p-toluene sulfonate,
diisopropyl-(2-oxopropyl)sulfonium p-toluene sulfonate,
diisopropyl-(2-oxobutyl)sulfonium p-toluene sulfonate,
diisopropyl-(2-oxopentyl)sulfonium p-toluene sulfonate,
diisopropyl-(2-oxohexyl)sulfonium p-toluene sulfonate,
diisopropyl-(2-oxoheptyl)sulfonium p-toluene sulfonate,
diisopropyl-(2-oxooctyl)sulfonium p-toluene sulfonate,
diisopropyl-(3-methyl-2-oxobutyl)sulfonium p-toluene sulfonate,
3,3-dimethyl-2-oxobutyl diisopropylsulfonium p-toluene sulfonate,
2-cyclohexyl-2-oxoethyl diisopropylsulfonium p-toluene sulfonate,
2-cyclopentyl-2-oxoethyl diisopropylsulfonium p-toluene sulfonate,
tert-butyl methyl(2-oxopropyl)sulfonium p-toluene sulfonate,
tert-butyl methyl(2-oxobutyl)sulfonium p-toluene sulfonate,
tert-butyl methyl(2-oxopentyl)sulfonium p-toluene sulfonate,
tert-butyl methyl(2-oxohexyl)sulfonium p-toluene sulfonate,
tert-butyl methyl(2-oxoheptyl)sulfonium p-toluene sulfonate,
tert-butyl methyl(2-oxooctyl)sulfonium p-toluene sulfonate,
tert-butyl methyl(3-methyl-2-oxobutyl )sulfonium p-toluene sulfonate,
tert-butyl(3,3-dimethyl-2-oxobutyl)methylsulfonium p-toluene sulfonate,
tert-butyl(2-cyclohexyl-2-oxoethyl)methylsulfonium p-toluene sulfonate,
tert-butyl(2-cyclopentyl-2-oxoethyl)methylsulfonium p-toluene sulfonate,
cyclohexyl methyl(2-oxopropyl)sulfonium p-toluene sulfonate,
cyclohexyl methyl(2-oxobutyl)sulfonium p-toluene sulfonate,
cyclohexyl methyl(2-oxopentyl)sulfonium p-toluene sulfonate,
cyclohexyl methyl(2-oxohexyl)sulfonium p-toluene sulfonate,
cyclohexyl methyl(2-oxoheptyl)sulfonium p-toluene sulfonate,
cyclohexylmethyl(2-oxooctyl)sulfonium p-toluene sulfonate,
cyclohexyl methyl(3-methyl-2-oxobutyl)sulfonium p-toluene sulfonate,
cyclohexyl(3,3-dimethyl-2-oxobutyl)methylsulfonium p-toluene sulfonate,
cyclohexyl(2-cyclohexyl-2-oxoethyl)methylsulfonium p-toluene sulfonate,
cyclohexyl(2-cyclopentyl-2-oxoethyl)methylsulfonium p-toluene sulfonate,
2-oxopropyl thiacyclopentanium p-toluene sulfonate,
2-oxobutyl thiacyclopentanium p-toluene sulfonate,
2-oxopentyl thiacyclopentanium p-toluene sulfonate,
2-oxohexyl thiacyclopentanium p-toluene sulfonate,
2-oxoheptyl thiacyclopentanium p-toluene sulfonate,
2-oxooctyl thiacyclopentanium p-toluene sulfonate,
3 -methyl-2-oxobutyl thiacyclopentanium p-toluene sulfonate,
3 3-dimethyl-2-oxobutyl thiacyclopentanium p-toluene sulfonate,
2-cyclohexyl-2-oxoethyl thiacyclopentanium p-toluene sulfonate,
2-cyclopentyl-2-oxoethyl thiacyclopentanium p-toluene sulfonate,
2-oxopropyl thiacyclohexanium p-toluene sulfonate,
2-oxobutyl thiacyclohexanium p-toluene sulfonate,
2-oxopentyl thiacyclohexanium p-toluene sulfonate, 2-oxohexyl thiacyclohexanium p-toluene sulfonate,
2-oxoheptyl thiacyclohexanium p-toluene sulfonate,
2-oxooctyl thiacyclohexanium p-toluene sulfonate,
3-methyl-2-oxobutyl thiacyclohexanium p-toluene sulfonate,
3,3-dimethyl-2-oxobutyl thiacyclohexanium p-toluene sulfonate,
2-cyclohexyl-2-oxoethyl thiacyclohexanium p-toluene sulfonate,
2-cyclopentyl-2-oxoethyl thiacyclohexanium p-toluene sulfonate,
2-oxopropyl(1,4-thioxanium)p-toluene sulfonate,
2-oxobutyl(1,4-thioxanium)p-toluene sulfonate,
2-oxopentyl(1,4-thioxanium)p-toluene sulfonate,
2-oxohexyl(1,4-thioxanium)p-toluene sulfonate,
2-oxoheptyl(1,4-thioxanium)p-toluene sulfonate,
2-oxooctyl(1,4-thioxanium)p-toluene sulfonate,
3-methyl-2-oxobutyl(1,4-thioxanium)p-toluene sulfonate,
3,3-dimethyl-2-oxobutyl(1,4-thioxanium)p-toluene sulfonate,
2-cyclohexyl-2-oxoethyl(1,4-thioxanium)p-toluene sulfonate,
2-cyclopentyl-2-oxoethyl(1,4-thioxanium)p-toluene sulfonate,
2-oxopropyl(4-oxothiacyclohexanium)p-toluene sulfonate,
2-oxobutyl(4-oxothiacyclohexanium)p-toluene sulfonate,
2-oxopentyl(4-oxothiacyclohexanium)p-toluene sulfonate,
2-oxohexyl(4-oxothiacyclohexanium)p-toluene sulfonate,
2-oxoheptyl(4-oxothiacyclohexanium)p-toluene sulfonate,
2-oxooctyl(4-oxothiacyclohexanium)p-toluene sulfonate,
3-methyl-2-oxobutyl(4-oxothiacyclohexanium)p-toluene sulfonate,
3,3-dimethyl-2-oxobutyl(4-oxothiacyclohexanium)p-toluene sulfonate,
2-cyclohexyl-2-oxoethyl(4-oxothiacyclohexanium)p-toluene sulfonate,
2-cyclopentyl-2-oxoethyl(4-oxothiacyclohexanium) p-toluene sulfonate,
2-oxopropyl(1,4-dithianium)p-toluene sulfonate,
2-oxobutyl(1,4-dithianium)p-toluene sulfonate,
2-oxopentyl(1,4-dithianium)p-toluene sulfonate,
2-oxohexyl(1,4-dithianium)p-toluene sulfonate,
2-oxoheptyl(1,4-dithianium)p-toluene sulfonate,
2-oxooctyl(1,4-dithianium)p-toluene sulfonate,
3-methyl-2-oxobutyl(1,4-dithianium)p-toluene sulfonate,
3,3-dimethyl-2-oxobutyl(1,4-dithianium)p-toluene sulfonate,
2-cyclohexyl-2-oxoethyl(1,4-dithianium)p-toluene sulfonate,
2-cyclopentyl-2-oxoethyl(1,4-dithianium)p-toluene sulfonate,
2-oxocyclohexyl thiacyclopentanium p-toluene sulfonate,
dimethyl-(2-oxopropyl)sulfonium camphor sulfonate,
dimethyl-(2-oxobutyl)sulfonium camphor sulfonate,
dimethyl-(2-oxopentyl)sulfonium camphor sulfonate,
dimethyl-(2-oxohexyl)sulfonium camphor sulfonate,
dimethyl-(2-oxoheptyl)sulfonium camphor sulfonate,
dimethyl-(2-oxooctyl)sulfonium camphor sulfonate,
dimethyl-(3-methyl-2-oxobutyl)sulfonium camphor sulfonate,
3,3-dimethyl-2-oxobutyl dimethylsulfonium camphor sulfonate,
2-cyclohexyl-2-oxoethyl dimethylsulfonium camphor sulfonate,
2-cyclopentyl-2-oxoethyl dimethylsulfonium camphor sulfonate,
diethyl-(2-oxopropyl)sulfonium camphor sulfonate,
diethyl-(2-oxobutyl)sulfonium camphor sulfonate,
diethyl-(2-oxopentyl)sulfonium camphor sulfonate,
diethyl-(2-oxohexyl)sulfonium camphor sulfonate,
diethyl-(2-oxoheptyl)sulfonium camphor sulfonate,
diethyl-(2-oxooctyl)sulfonium camphor sulfonate,
diethyl-(3-methyl-2-oxobutyl)sulfonium camphor sulfonate,
3,3-dimethyl-2-oxobutyl diethylsulfonium camphor sulfonate,
2-cyclohexyl-2-oxoethyl diethylsulfonium camphor sulfonate,
2-cyclopentyl-2-oxoethyl diethylsulfonium camphor sulfonate,
dibutyl-(2-oxopropyl)sulfonium camphor sulfonate,
dibutyl-(2-oxobutyl)sulfonium camphor sulfonate,
dibutyl-(2-oxopentyl)sulfonium camphor sulfonate,
dibutyl-(2-oxohexyl)sulfonium camphor sulfonate,
dibutyl-(2-oxoheptyl)sulfonium camphor sulfonate,
dibutyl-(2-oxooctyl)sulfonium camphor sulfonate,
dibutyl-(3-methyl-2-oxobutyl)sulfonium camphor sulfonate,
dibutyl-(3,3-dimethyl-2-oxobutyl)sulfonium camphor sulfonate,
dibutyl-(2-cyclohexyl-2-oxoethyl)sulfonium camphor sulfonate,
dibutyl-(2-cyclopentyl-2-oxoethyl)sulfonium camphor sulfonate,
diisopropyl-(2-oxopropyl)sulfonium camphor sulfonate,
diisopropyl-(2-oxobutyl)sulfonium camphor sulfonate,
diisopropyl-(2-oxopentyl)sulfonium camphor sulfonate,
diisopropyl-(2-oxohexyl)sulfonium camphor sulfonate,
diisopropyl-(2-oxoheptyl)sulfonium camphor sulfonate,
diisopropyl-(2-oxooctyl)sulfonium camphor sulfonate,
diisopropyl-(3-methyl-2-oxobutyl)sulfonium camphor sulfonate,
3,3-dimethyl-2-oxobutyl diisopropylsulfonium camphor sulfonate,
2-cyclohexyl-2-oxoethyl diisopropylsulfonium camphor sulfonate,
2-cyclopentyl-2-oxoethyl diisopropylsulfonium camphor sulfonate,
tert-butyl methyl(2-oxopropyl)sulfonium camphor sulfonate,
tert-butyl methyl(2-oxobutyl)sulfonium camphor sulfonate.
tert-butyl methyl(2-oxopentyl)sulfonium camphor sulfonate,
tert-butyl methyl(2-oxohexyl)sulfonium camphor sulfonate,
tert-butyl methyl(2-oxoheptyl)sulfonium camphor sulfonate,
tert-butyl methyl(2-oxooctyl)sulfonium camphor sulfonate,
tert-butyl methyl(3-methyl-2-oxobutyl)sulfonium camphor sulfonate,
tert-butyl(3,3-dimethyl-2-oxobutyl)methylsulfonium camphor sulfonate,
tert-butyl(2-cyclohexyl-2-oxoethyl)methylsulfonium camphor sulfonate,
tert-butyl(2-cyclopentyl-2-oxoethyl)methylsulfonium camphor sulfonate,
cyclohexyl methyl(2-oxopropyl)sulfonium camphor sulfonate,
cyclohexyl methyl(2-oxobutyl)sulfonium camphor sulfonate,
cyclohexyl methyl(2-oxopentyl)sulfonium camphor sulfonate,
cyclohexyl methyl(2-oxohexyl)sulfonium camphor sulfonate,
cyclohexyl methyl(2-oxoheptyl)sulfonium camphor sulfonate, cyclohexyl methyl(2-oxooctyl)sulfonium camphor sulfonate,
cyclohexyl methyl(3-methyl-2-oxobutyl)sulfonium camphor sulfonate,
cyclohexyl(3,3-dimethyl-2-oxobutyl)methylsulfonium camphor sulfonate,
cyclohexyl(2-cyclohexyl-2-oxoethyl)methylsulfonium camphor sulfonate,
cyclohexyl(2-cyclopentyl-2-oxoethyl)methylsulfonium camphor sulfonate,
2-oxopropyl thiacyclopentanium camphor sulfonate,
2-oxobutyl thiacyclopentanium camphor sulfonate,
2-oxopentyl thiacyclopentanium camphor sulfonate,
2-oxohexyl thiacyclopentanium camphor sulfonate,
2-oxoheptyl thiacyclopentanium camphor sulfonate,
2-oxooctyl thiacyclopentanium camphor sulfonate,
3-methyl-2-oxobutyl thiacyclopentanium camphor sulfonate,
3,3-dimethyl-2-oxobutyl thiacyclopentanium camphor sulfonate,
2-cyclohexyl-2-oxoethyl thiacyclopentanium camphor sulfonate,
2-cyclopentyl-2-oxoethyl thiacyclopentanium camphor sulfonate,
2-oxopropyl thiacyclohexanium camphor sulfonate,
2-oxobutyl thiacyclohexanium camphor sulfonate,
2-oxopentyl thiacyclohexanium camphor sulfonate,
2-oxohexyl thiacyclohexanium camphor sulfonate,
2-oxoheptyl thiacyclohexanium camphor sulfonate,
2-oxooctyl thiacyclohexanium camphor sulfonate,
3-methyl-2-oxobutyl thiacyclohexanium camphor sulfonate,
3,3-dimethyl-2-oxobutyl thiacyclohexanium camphor sulfonate,
2-cyclohexyl-2-oxoethyl thiacyclohexanium camphor sulfonate,
2-cyclopentyl-2-oxoethyl thiacyclohexanium camphor sulfonate,
2-oxopropyl(1,4-thioxanium)camphor sulfonate,
2-oxobutyl(1,4-thioxanium)camphor sulfonate,
2-oxopentyl(1,4-thioxanium)camphor sulfonate,
2-oxohexyl(1,4-thioxanium)camphor sulfonate,
2-oxoheptyl(1,4-thioxanium)camphor sulfonate,
2-oxooctyl(1,4-thioxanium)camphor sulfonate,
3-methyl-2-oxobutyl(1,4-thioxanium)camphor sulfonate,
3,3-dimethyl-2-oxobutyl(1,4-thioxanium)camphor sulfonate,
2-cyclohexyl-2-oxoethyl(1,4-thioxanium)camphor sulfonate,
2-cyclopentyl-2-oxoethyl (1,4-thioxanium)camphor sulfonate,
2-oxopropyl(4-oxothiacyclohexanium)camphor sulfonate,
2-oxobutyl(4-oxothiacyclohexanium)camphor sulfonate,
2-oxopentyl (4-oxothiacyclohexanium)camphor sulfonate,
2-oxohexyl (4-oxothiacyclohexanium)camphor sulfonate,
2-oxoheptyl(4-oxothiacyclohexanium)camphor sulfonate,
2-oxooctyl(4-oxothiacyclohexanium)camphor sulfonate,
3-methyl-2-oxobutyl(4-oxothiacyclohexanium)camphor sulfonate,
3,3-dimethyl-2-oxobutyl(4-oxothiacyclohexanium)camphor sulfonate,
2-cyclohexyl-2-oxoethyl(4-oxothiacyclohexanium)camphor sulfonate,
2-cyclopentyl-2-oxoethyl(4-oxothiacyclohexanium) camphor sulfonate,
2-oxopropyl(1,4-dithianium)camphor sulfonate,
2-oxobutyl(1,4-dithianium)camphor sulfonate,
2-oxopentyl(1,4-dithianium)camphor sulfonate,
2-oxohexyl (1,4-dithianium)camphor sulfonate,
2-oxoheptyl(1,4-dithianium)camphor sulfonate,
2-oxooctyl(1,4-dithianium)camphor sulfonate,
3-methyl-2-oxobutyl(1,4-dithianium)camphor sulfonate,
3,3-dimethyl-2-oxobutyl(1,4-dithianium)camphor sulfonate,
2-cyclohexyl-2-oxoethyl(1,4-dithianium)camphor sulfonate,
2-cyclopentyl-2-oxoethyl(1,4-dithianium)camphor sulfonate, and
2-oxocyclohexyl thiacyclopentanium camphor sulfonate, By the addition the sulfonium salt represented by the formula (I), the line edge roughness can be improved. With a resist composition using the sulfonium salt represented by the formula (I) singly as an acid generator, it becomes difficult to obtain sufficient sensitivity and resolution. Then, in the resist composition of the present invention, at least one onium salt selected from the formulae (IIa) and (IIb) is used in combination with such a sulfonium salt of the formula (I) as an acid generator. By using such an onium salt-based acid generator in combination therewith, it is possible to improve the sensitivity and the resolution as compared with the case where the sulfonium salt-based acid generator of the formula (I) is used singly, and it is possible to improve the line edge roughness as compared with the case where at least one onium salt-based acid generator selected from the formulae (IIa) and (IIb) is used singly.

In the formulae (IIa) and (IIb) each respectively representing triphenylsulfonium salt and diphenyliodonium salt, $P^1$, $P^2$, $P^3$, $P^4$, and $P^5$ each independently represent hydrogen, a hydroxyl group, an alkyl group having from 1 to 6 carbon atoms, or an alkoxy group having from 1 to 6 carbon atoms. The alkyl group and the alkoxy group may be straight chain or branched when they each have 3 or more carbon atoms. Specific examples of an alkyl group include methyl group, ethyl group, propyl group, isopropyl group, butyl group, tert-butyl group, pentyl group, and hexyl group. Examples of the alkoxy group include methoxy group, ethoxy group, propoxy group, and butoxy group. Whereas, in the formulae (IIa) and (IIb), $P^6SO_3^-$ and $P^7SO_3^-$ each forming an anion represent an organosulfonate ion. $P^6$ and $P^7$ each may be an organic group having about from 1 to 12 carbon atoms. Examples thereof include a perfluoroalkyl group having from 1 to 8 carbon atoms, an alkyl group having from 1 to 8 carbon atoms, an aromatic group having from 6 to 12 carbon atoms and a camphor group. Specific examples of the perfluoroalkyl group having from 1 to 8 carbon atoms, the alkyl group having from 1 to 8 carbon atoms, and the aromatic group having from 6 to 12 carbon atoms include the same ones as described above.

If there is a commercially available product of the triphenylsulfonium salt represented by the formula (IIa) or the diphenyliodonium salt represented by the formula (IIb), it may be used as it is. Alternatively, it may be produced in accordance with the conventional method. The triphenylsulfonium salt (IIa) may be produced by the following methods, for example:

a method in which the corresponding triphenylsulfonium bromide is allowed to react with a silver salt of the sulfonic acid having the same anion as the anion of the objective compound;

a method in which the corresponding diphenylsulfoxide, a benzene compound, and a perfluoroalkanesulfonic acid are allowed to mutually react in the presence of a trifluoroacetic acid anhydride in accordance with the description in "Chem. pharm. Bull.", Vol.29, 3753 (1981);

a method in which the corresponding aryl Grignard reagent is allowed to react with thionyl chloride, and then the reaction product is allowed to react with triorganosilyl halide to prepare a triarylsulfonium halide, which is then allowed to react with the silver salt of the sulfonic acid having the same anion as the anion of the objective compound in accordance with the description in JP-A-8-311018; and the like. Whereas, the compound of the formula (IIa) wherein $P^1$, $P^2$, and/or $P^3$ is a hydroxyl group can be produced by treating the triphenylsulfonium salt having a tert-butoxy group on the benzene ring with the sulfonic acid having the same anion as the anion of the compound, and eliminating the tert-butoxy group therefrom in accordance with the description in JP-A-8-311018.

Whereas, the diphenyliodonium salt (IIb) can be produced with the following methods, for example;

a method in which an iodyl sulfuric acid and the corresponding aryl compound are allowed to react, followed by the addition of the sulfonic acid having the same anion as the anion of the objective compound in accordance with the description in "J. Am. Chem. Soc.", vol.81, 342 (1959);

a method in which iodine and a trifluoroacetic acid are added in a mixed solution of an acetic acid anhydride and a fuming nitric acid to obtain a reaction product, which is then reacted with the corresponding aryl compound, followed by the addition of a sulfonic acid having the same anion as the anion of the objective compound;

a method in which to a mixture of the corresponding aryl compound, an acetic anhydride, and potassium iodate, is added dropwise a concentrated sulfuric acid, followed by the addition of the sulfonic acid having the same anion as the anion of the objective compound in accordance with the description in JP-A-9-179302.

Examples of the triphenylsulfonium salt represented by the formula (IIa) and diphenyliodonium salt represented by the formula (IIb) include:
triphenylsulfonium methanesulfonate,
triphenylsulfonium ethanesulfonate,
triphenylsulfonium butanesulfonate,
triphenylsulfonium perfluorobutanesulfonate,
triphenylsulfonium p-toluenesulfonate,
triphenylsulfonium camphor sulfonate,
4-methylphenyldiphenylsulfonium methanesulfonate,
4-methylphenyldiphenylsulfonium ethanesulfonate,
4-methylphenyldiphenylsulfonium butanesulfonate,
4-methylphenyldiphenylsulfonium benzensulfonate,
4-methylphenyldiphenylsulfonium p-toluenesulfonate,
4-methylphenyldiphenylsulfonium camphor sulfonate,
4-methylphenyldiphenylsulfonium perfluorobutanesulfonate,
4-hydroxyphenyldiphenylsulfonium perfluorobutanesulfonate,
4-methoxyphenyldiphenylsulfonium perfluorooctanesulfonate,
tris(4-methylphenyl)sulfonium perfluorooctanesulfonate,
tri(4-methoxyphenyl)sulfonium perfluorooctanesulfonate,
4-methylphenyldiphenylsulfonium perfluorooctanesulfonate,
4-hydroxyphenyldiphenylsulfonium perfluorooctanesulfonate,
4-methoxyphenyldiphenylsulfonium perfluorooctanesulfonate,
tris(4-methylphenyl)sulfonium perfluorooctanesulfonate,
tris(4-methoxyphenyl)sulfonium perfluorooctanesulfonate,
diphenyl iodonium perfluorobutanesulfonate,
di(4-methoxyphenyl)iodonium perfluorooctanesulfonate,
di(4-tert-butylphenyl)iodonium perfluorooctanesulfonate,
di(4-tert-butylphenyl)iodonium methanesulfonate,
di(4-tert-butylphenyl)iodonium ethanesulfonate,
di(4-tert-butylphenyl)iodonium butanesulfonate,
di(4-tert-butylphenyl)iodonium benzensulfonate,
di(4-tert-butylphenyl)iodonium p-toluenesulfonate, and
di(4-tert-butylphenyl)iodonium camphor sulfonate.

Then, the resin component constituting the resist composition of the present invention will be described. The resin has a polymerization unit having a group unstable against an acid. The resin for a chemically amplifying type positive resist itself is generally alkali-insoluble, or alkali-slightly soluble. However, a part of the groups are cleaved by the action of the acid, and the resin becomes alkali-soluble after cleavage. The groups unstable against an acid in the present invention may also be such various ones known in the art. As the groups unstable against an acid, specifically, various esters of a carboxylic acid can be exemplified. Example of the esters of carboxylic acid include alkyl esters such as methyl ester and tert-butyl ester, acetal type esters such as methoxymethyl ester, ethoxymethyl ester, 1-ethoxyethyl ester, 1-isobutoxyethyl ester, 1-isopropoxyethyl ester, 1-ethoxypropyl ester, 1-(2-methoxyethoxy)ethyl ester, 1-(2-acetoxyethoxy)ethyl ester, 1-[2-(1-adamantyloxy)ethoxy]ethyl ester, 1-[2-(1-adamantanecarbonyloxy)ethoxy]ethyl ester, tetrahydro-2-furylester, and tetrahydro-2-pyranylester, and alicyclic esters such as isobornyl ester, 2-alkyl-2-adamantyl ester, and 1-(1-adamantyl)-1-alkylalkyl ester. Monomers leading to polymerization units having such carboxylic acid esters may be the ones of (meth)acrylate type such as methacrylic acid ester and acrylic acid ester, or the one in which a carboxylic acid ester group is bonded to an alicyclic monomer, such as norbornenecarboxylic acid ester, tricyclodecenecarboxylic acid ester, or tetracyclodecenecarboxylic acid ester.

Among such monomers, the monomers having a bulky group including an alicyclic one such as 2-alkyl-2-adamanyl or 1-(1-adamantyl)-1-alkylalkyl as the group which is cleaved by the action of an acid is preferably used because of the excellent resolution. Examples of such monomers containing a bulky group include (meth)acrylic acid-2-alkyl-2-adamantyl, (meth)acrylic acid 1-(1-adamantyl)-1-alkylalkyl, 5-norbornene-2-carboxylic acid 2-alkyl-2-adamantyl, and 5-norbornene-2-carboxylic acid 1-(1-adamantyl)-1-alkylalkyl. Among them, (meth)acrylic acid-2-alkyl-2-adamantyl is preferably used as the monomer because of the excellent resolution. Typical examples of such (meth)acrylic-2-alkyl-acid 2-adamantyl include acrylic acid-2-methyl-2-adamantyl, methacrylic acid-2-methyl-2-adamantyl, acrylic acid-2-ethyl-2-adamantyl, methacrylic acid-2-ethyl-2-adamantyl, and acrylic acid-2-n-butyl-2-adamantyl. Among them, (meth)acrylic acid-2-ethyl-2-adamantyl is particularly preferably used because of the good balance between the sensitivity and the heat resistance. If required, other monomers having a group which is cleaved by the action of an acid may also be used in combination.

(Meth)acrylic acid 2-alkyl-2-adamantyl can be generally produced by the reaction between 2-alkyl-adamantanol or a metal salt thereof, and an acrylic acid halide or a methacrylic acid halide.

The resin specified in the present invention may further contain, in addition to the polymerization unit having a group instable against an acid as described above, another polymerization unit which is not cleaved, or is less likely to be cleaved by the action of an acid. Examples of the other polymerization unit which can be contained therein include a polymerization unit having a free carboxylic acid group such as an acrylic acid or a methacrylic acid, a polymerization unit of an aliphatic unsaturated dicarboxylic acid anhydride such as a maleic acid anhydride or an itaconic acid anhydride, a polymerization unit of 2-norbornene, a polymerization unit of (meth)acrylonitrile, and polymerization units of various (meth)acrylic acid esters. The polymerization unit of hydroxystyrene is not preferred for ArF exposure because the amount of light absorption is large, but it is preferably used for KrF exposure because there occurs no problem of light absorption.

Particularly, it is preferable in terms of the adhesion of the resist to a substrate that at least one polymerization units selected from a polymerization unit of p-hydroxystyrene; a polymerization unit of m-hydroxystyrene; a polymerization unit of (meth)acrylic acid 3-hydroxy-1-adamantyl; a a polymerization unit of (meth)acrylic acid 3,5-hydroxy-1-adamantyl; a polymerization unit of (meth)acryloyloxy-γ-butyrolactone in which the lactone ring may be substituted by alkyl; polymerization units of alicyclic lactones each represented by the following formulae (IIIa) and (IIIb):

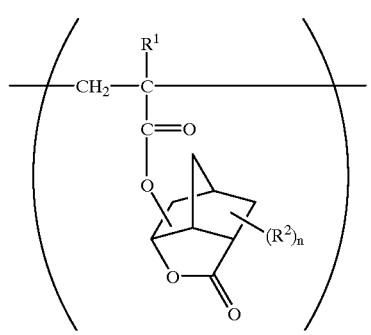

(IIIa)

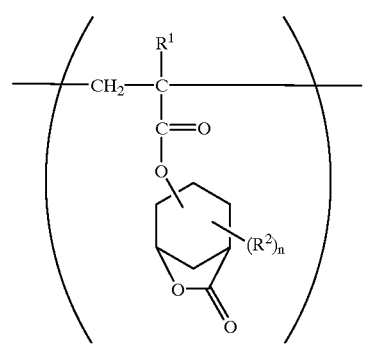

(IIIb)

wherein $R^1$ and $R^2$ each independently represent hydrogen or methyl, and n represents a number of from 1 to 3; and the like is copolymerized.

The (meth)acrylic acid 3-hydroxy-1-adamantyl, (meth) acrylic acid 3,5-dihydroxy-1-adamantyl are commercially available. Alternatively, they can also be produced by, for example, reacting the corresponding hydroxyadamantane with a (meth)acrylic acid or a halide thereof. Whereas, the (meth)acryloyloxy-γ-butyrolactone can be produced by reacting α-, or β-bromo-γ-butyrolactone in which the lactone ring may be substituted by alkyl with an acrylic acid or a methacrylic acid, or reacting α-, or β-hydroxy-γ-butyrolactone in which the lactone ring may be substituted by alkyl with an acrylic acid halide or a methacrylic acid halide. As the monomers leading to the polymerization units of alicyclic lactones each represented by the formula (IIIa) and (IIIb), for example, (meth)acrylic acid esters of alicyclic lactones having a hydroxyl group, mixtures thereof, such as those shown below and the like can be mentioned. These esters can be produced, for example, by the reaction between the corresponding alicyclic lactone having a hydroxyl group and (meth)acrylic acids (ex., JP-A-2000-26446).

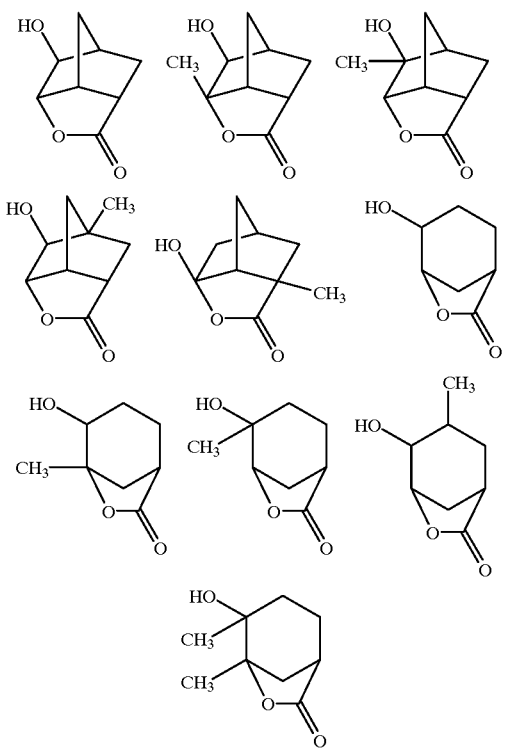

Any of the polymerization units of (meth)acrylic acid 3-hydroxy-1-adamantyl, and the polymerization units of (meth)acrylic acid 3,5-dihydroxy-1-adamantyl, the polymerization units of α-(meth)acryloyloxy-γ-butyrolactone and the polymerization units of β-(meth)acryloyloxy -γ-butyrolactone, and the polymerization units of alicyclic lactones represented by the formulae (IIIa) or (IIIb) has a high polarity. The presence of any of them in a resin improves the adhesion of a resist containing it to a substrate. These polymerization units also contributes to the improvement of the resolution of the resist.

Examples of the monomers leading to the polymerization units of (meth)acryloyloxy-γ-butyrolactone include α-acryloyloxy -γ-butyrolactone, α-methacryloyloxy-γ-butyrolactone, α-acryloyloxy-β, β-dimethyl-γ-butyrolactone, α-methacryloyloxy-β, β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone, and β-methacryloyloxy-α-methyl-γ-butyrolactone.

For KrF excimer laser exposure, even if the polymerization unit of hydroxystyrene is used as the polymerization unit of a resin, sufficient transmittance can be obtained. Specifically, p-, or m-hydroxystylene copolymer resins as shown below can be mentioned as such resins. Each of such copolymer resins can be obtained by radical polymerizing the corresponding (meth)acrylic acid ester monomers, acetoxystyrene, and styrene, followed by deacetylation by an acid.
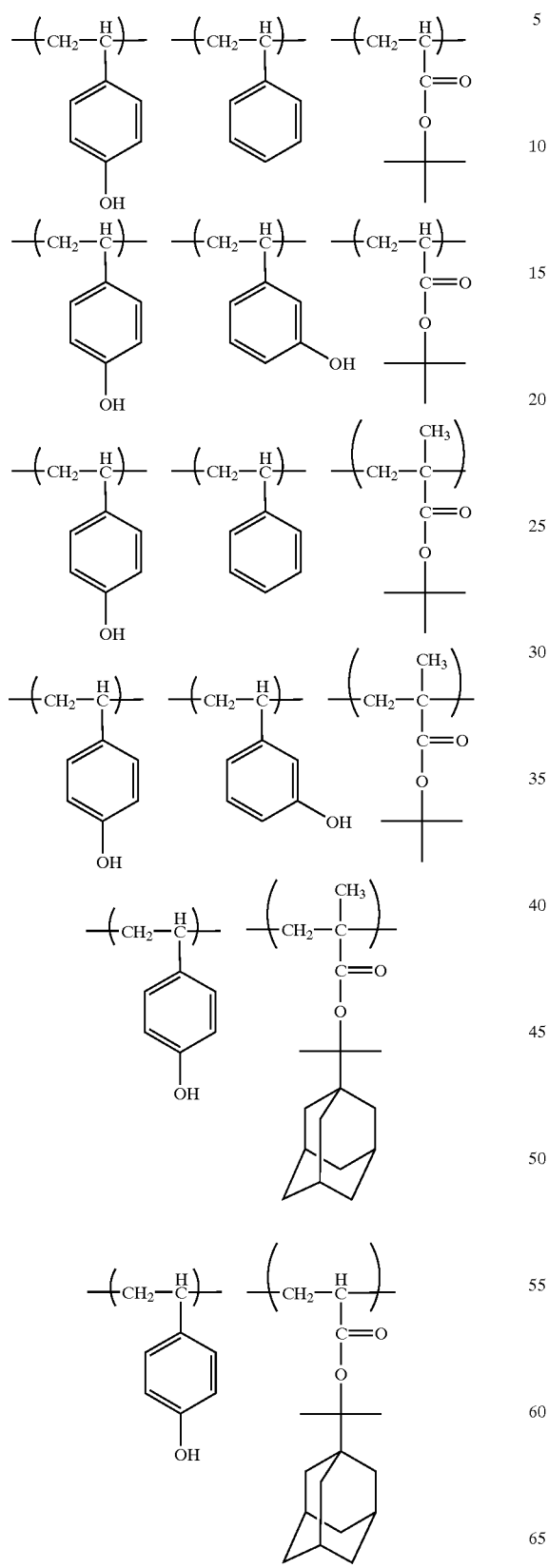
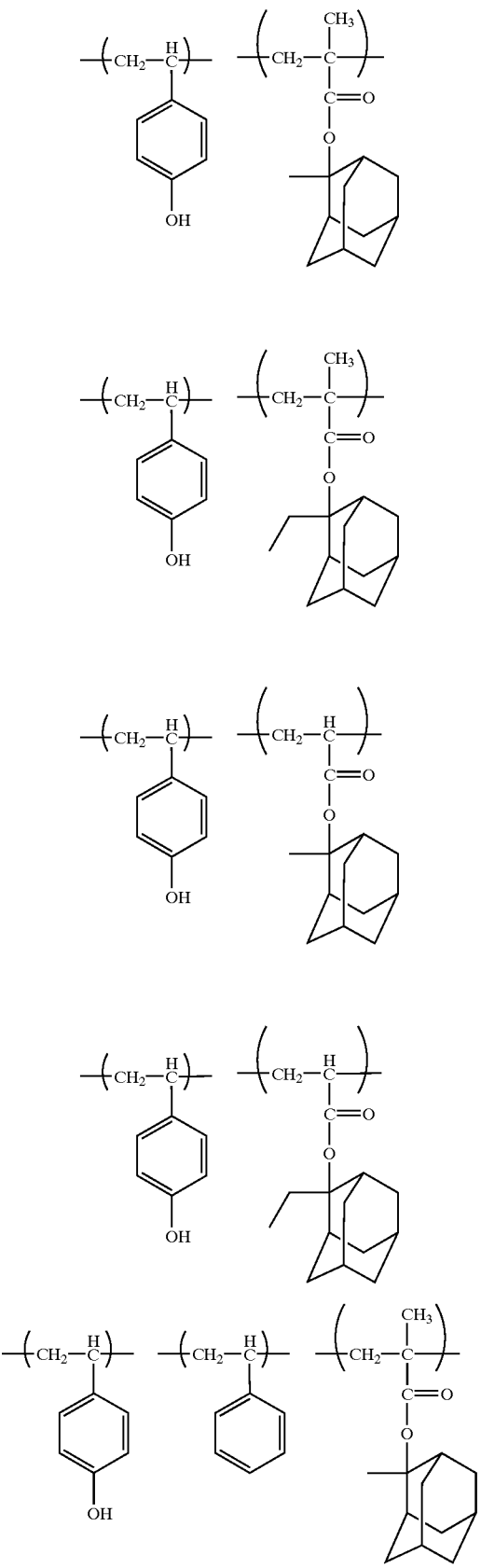

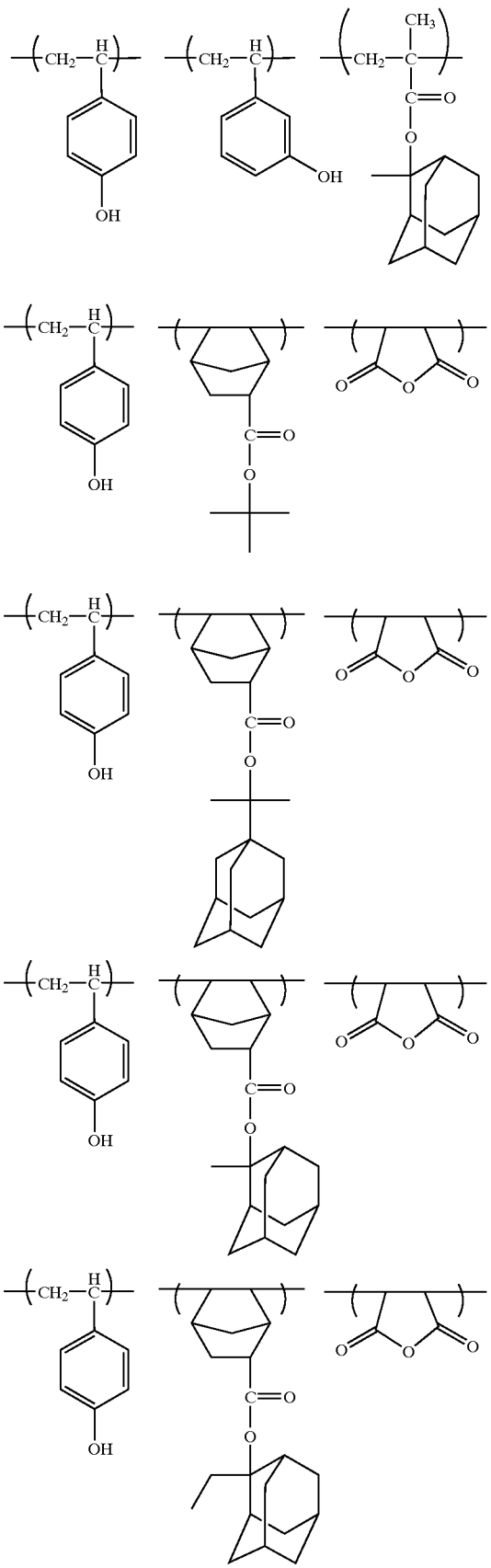

In these cases, use of 2-alkyl-2-adamantyl or 1-adamantyl-1-alkylalkyl as the group instable against an acid is more advantageous in terms of the dry etching resistance.

Further, the resin containing the polymerization unit of 2-norbornene has a strong structure because it has an alicyclic group directly on its main chain, and hence it exhibits an excellent dry etching resistance characteristic. The polymerization unit of 2-norbornene can be introduced into the main chain by radical polymerization using a corresponding 2-norbornene and an aliphatic unsaturated dicarboxylic acid anhydrides such as maleic acid anhydride and itaconic acid anhydride in combination. Therefore, the polymerization unit of 2-norbornene is formed by cleavage of its double bond, and may be represented by the formula (IV). Further, the polymerization unit of a maleic acid anhydride and the polymerization unit of an itaconic acid anhydride, which are the polymerization units of aliphatic unsaturated dicarboxylic acid anhydrides, are formed by cleavage of their respective double bonds, and maybe represented by the formulae (V) and (VI), respectively.

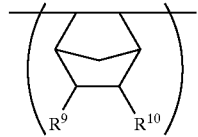
(IV)

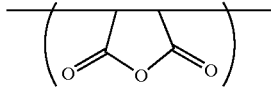
(V)

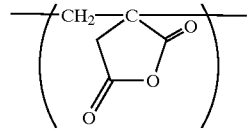
(VI)

In the formula (IV), $R^3$ and $R^4$ each independently represent hydrogen, alkyl having from 1 to 3 carbon atoms, hydroxyalkyl having from 1 to 3 carbon atoms, carboxyl, cyano, or —COOZ (Z is an alcohol residue) group, or $R^3$ and $R^4$ may both together form a carboxylic acid anhydride residue represented by —C(=O)OC(=O)—. When $R^3$ and/or $R^4$ is alkyl, specific examples thereof include methyl, ethyl, and propyl. Specific examples of hydroxyalkyl as $R^3$ or $R^4$ include hydroxymethyl and 2-hydroxyethyl. When $R^3$ and/or $R^4$ is a —COOZ group, it is formed by esterifying carboxyl. As the alcohol residues corresponding to Z, for example, alkyl having about from 1 to 8 carbon atoms which may be substituted, 2-oxooxolan-3-, or -4-yl, and the like can be mentioned. Herein, as the substituents for the alkyl, a hydroxyl group, alicyclic hydrocarbon residues, and the like can be exeplified. Then, when $R^3$ and/or $R^4$ is a carboxylic acid ester residue represented by —COOZ, specific examples thereof include methoxycarbonyl, ethoxycarbonyl, 2-hydroxyethoxycarbonyl, tert-butoxycarbonyl, 2-oxooxolan-3-yloxycarbonyl, 2-oxooxolan-4-yloxycarbonyl, 1,1,2-trimethylpropoxycarbonyl, 1-cyclohexyl-1-methylethoxycarbonyl, 1-(4-methylcyclohexyl)-1-methylethoxycarbonyl, and 1-(1-adamantyl)-1-methylethoxycarbonyl.

Examples of the monomers for deriving 2-norbornene represented by the formula (IV) include:

2-norbornene,
2-hydroxy-5-norbornene,
5-norbornene-2-carboxylic acid,
5-norbornene-2-methylcarboxylate,
5-norbornene-2-t-butylcarboxylate,
5-norbornene-2-(1-cyclohexyl-1-methylethyl)carboxylate,
5-norbornene-2-[1-(4-methylcyclohexyl)-1-methylethyl] carboxylate,
5-norbornene-2-[1-(4-hydroxycyclohexyl)-1-methylethyl] carboxylate,
5-norbornene-2-[1-methyl-1-(4-oxocyclohexyl)-ethyl] carboxylate,
5-norbornene-2-[1-(1-adamantyl)-1-methylethyl] carboxylate,
5-norbornene-2-(1-methylcyclohexyl)carboxylate,
5-norbornene-2-(2-methyl-2-adamantyl)carboxylate,
5-norbornene-2-(2-ethyl-2-adamantyl)carboxylate,
5-norbornene-2-(2-hydroxy-1-ethyl)carboxylate,
5-norbornene-2-methanol, and
5-norbornene-2,3-dicarboxylic acid anhydride.

It is preferable that the resin to be used in the present invention generally contains the polymerization unit having a group unstable against an acid in an amount in the range of from 10 to 80 mol % although the amount varies according to the kind of radiation for patterning exposure, the kind of the group instable against an acid, etc. When the polymerization unit of (meth)acrylic acid 2-alkyl-2-adamantyl or (meth)acrylic acid 1-(1-adamantyl)-1-alkylalkyl is used as the group unstable against an acid, it is advantageous that this unit is contained in an amount of not less than 15 mol % based on the total amount of the resin. Further, when in addition to the polymerization unit unstable against an acid, other polymerization units which are less likely to be cleaved by the action of an acid, such as the polymerization units of (meth)acrylic acid 3-hydroxy-1-adamantyl, the polymerization units of (meth)acrylic acid 3,5-hydroxy-1-adamantyl and α-methacryloyloxy-γ-butyrolactone, the polymerization unit of β-methacryloyloxy-γ-butyrolactone, the polymerization units of alicyclic lactones represented by the formulae (IIIa) or (IIIb), the polymerization unit of hydroxystyrene, the polymerization unit of 2-norbornene represented by the formula (IV), the polymerization unit of maleic acid anhydride represented by the formula (V) and the polymerization unit of itaconic acid anhydride represented by the formula (VI), are present therein, the total amount thereof is preferably in the range of from 20 to 90 mol % based on the total amount of the resin.

When 2-norbornes and aliphatic unsaturated dicarboxylic acid anhydrides are used as copolymerization monomers, since they tend to be difficult to polymerize, they are preferably used in excess amounts in consideration of this point.

It is also known that, generally in a chemical amplifying type positive resist composition, performance deterioration due to the deactivation of an acid associated with leaving after exposure can be reduced by adding basic compounds, especially basic nitrogen-containing organic compounds such as amines as quenchers. It is also preferable in the present invention that such basic compounds are added. Concrete examples of the basic compounds to be used as quenchers include the ones represented by the following formulae:

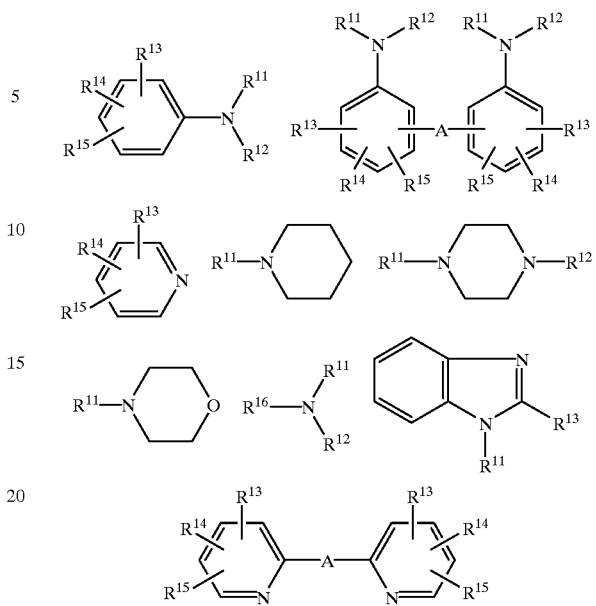

wherein $R^{11}$ and $R^{12}$, which are same or different from each other, represent hydrogen, or cycloalkyl, aryl or alkyl which may be optionally substituted with a hydroxyl; $R^{13}$, $R^{14}$ and $R^{15}$, which are same or different from each other, represent hydrogen, or cycloalkyl, aryl or alkyl which may be optionally substituted with a hydroxyl; $R^{16}$ represents cycloalkyl or alkyl which may be optionally substituted with a hydroxyl; and A represents alkylene, carbonyl, imino. The alkyl represented by $R^{11}$ to $R^{17}$ and alkoxy represented by $R^{13}$ to $R^{15}$ may have about 1 to 6 carbon atoms. The cycloalkyl represented by $R^{11}$ to $R^{16}$ may have about 5 to 10 carbon atoms and the aryl represented by $R^{11}$ to $R^{15}$ may have about 6 to 10 carbon atoms. The alkylene represented by A may have about 1 to 6 carbon atoms and may be straight-chained or branched.

The resist composition of the present invention preferably contains the resin in an amount in the range of 80 to 99.9% by weight, and the acid generator in an amount in the range of 0.1 to 20% by weight based on the total solid component weight of the resist composition. In the resist composition of the present invention, the amounts ratio of the sulfonium salt represented by the formula (I) to the onium salt selected from the triphenylsulfonium salt represented by the formula (IIa) and diphenyliodonium salt represented by the formula (IIb) is usually in the range of about 9:1 to 1:9 by weight, preferably 8:2 to 2:8, by weight.

When a basic compound is used as a quencher, it is preferably contained in an amount In the range of 0.01 to 1% by weight based on the total solid component weight of the resist composition. The composition may also contain, if required, small amount of various additives such as sensitizers, dissolution inhibitors, other resins, surfactants, stabilizers, and dyes so far as the objets of the present invention is not harmed.

The resist composition of the present invention generally becomes a resist solution in the state in which the above-described components are dissolved in a solvent to be applied on a substrate such as a silicon wafer by an usual method such as spin coating. The solvent herein used may be one which dissolves each component, has an appropriate drying rate, and provides a uniform and smooth coating after evaporation of the solvent, and can be one which is generally used in this field. Examples thereof Include glycol ether esters such as ethylcellosolve acetate, methylcellosolve acetate, and propylene glycolmonomethyl ether acetate; esters such as ethyl lactate, butyl acetate, amyl acetate, and ethyl pyruvate; ketones such as acetone, methyl isobutyl ketone, 2-heptanone, and cyclohexanone; and cyclic esters such as γ-butyrolactone. These solvents can be used alone or in combination of two or more thereof.

The resist film applied on a substrate, and dried is subjected to an exposure treatment for patterning. Then, after a heat-treatment for promoting a protecting deblocking reaction, development by an alkali developer is conducted. The alkali developer herein used can be various kinds of alkaline aqueous solutions used in this field. In general, an aqueous solution of tetramethylammoniumhydroxide or (2-hydroxyethyl)trimethylammoniumhydroxide (so-called colline) is often used.

The present invention will be described in more detail by way of examples, which should not be construed as limiting the scope of the present invention. All parts in examples are by weight unless otherwise stated. The weight-average molecular weight is a value determined from gel permeation chromatography using polystyrene as a reference standard.

Acid Generator Synthesis Example 1: Synthesis of Acid Generator B1

(1) Into a four-necked flask, were charged 70.17 parts of tetrahydrothiophene and 750 parts of acetone, to which 150 parts of 1-bromopinacolone was added dropwise, followed by stirring at room temperature for 24 hours. The precipitated crystal was collected by filtration, and washed with 100 parts of tert-butylmethyl ether, and dried to obtain 161.3 parts of 3,3-dimethyl-2-oxobutyl thiacyclopentanium bromide.

(2) Into a four-necked flask, were charged 80 parts of the 3,3-dimethyl-2-oxobutyl thiacyclopentanium bromide obtained in the step (1), and 3200 parts of acetonitrile, to which 56.33 parts of potassium trifluoromethanesulfonate was added dropwise, followed by stirring at room temperature for 18 hours. The precipitated potassium bromide was collected by filtration, and the filtrate was concentrated. Acetone was added thereto, followed by stirring at room temperature for 16 hours, and the insoluble matters were collected by filtration. The filtrate was further concentrated, and acetone was added thereto. Then, the mixture was charged in tert-butylmethyl ether, thereby to obtain 94.73 parts of the objective substance. This compound was found to be 3,3-dimethyl-2-oxobutyl thiacyclopentanium trlfluoromethanesulfonate represented by the following formula by $^1$H-NMR ("GX-270" manufactured by Nippon Denshi):

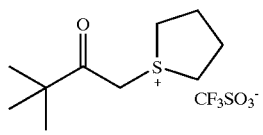

$^1$H-NMR (chloroform-d, internal standard substance tetramethylsilane): δ(ppm) 1.24 (s, 9H); 2.26–2.33 (m, 2H); 2.42–2.52 (m, 2H); 3.45–3.55 (m, 2H): 3.61–3.71 (m, 2H); 4.96 (s, 2H).

Acid Generator Synthesis Example 1-2; Synthesis of Acid Generator B1

(1) According to the same procedure as in Acid Generator Synthesis Example 1(1), except for increasing the reaction size, 3,3-dimethyl-2-oxobutylthiacyclopentanium bromide was obtained.

(2) Into a four-necked flask, were charged 169.58 parts of the 3,3-dimethyl-2-oxobutyl thiacyclopentanium bromide obtained in the step (1), and 3391.59 parts of acetonitrile, and the resulting mixture was cooled to 5° C. Thereto, 100 parts of trifluoromethanesulfonic acid was added dropwise, followed by stirring at 5° C. for 1.5 hours. Thereafter, the reaction mass was concentrated to 270 parts, to which 680 parts of ethyl actate was added. To the resulting mixture, 300 parts of tert-butylmethyl ether was added by stirring, and the precipitated matters were collected by filtration. The filter cake thus obtained was dissolved In 500 parts of ethyl actate, and, then, concentrated to 420 parts. Thereto, 50 parts of tert-butylmethyl ether was added by stirring, the precipitated matters were collected by filtration, and the precipitated matter was dried to obtain 156.22 parts of the objective substance.

Acid Generator Synthesis Examples 2 and 3; Synthesis of Acid Generators B2 and B3

Experiments were carried out in the same manner as in the step (2) of Acid Generator Synthesis Example 1, except that potassium perfluorobutanesulfonate and potassium perfluorooctanesulfonate were used in place of the potassium trifluoromethanesulfonate in the step (2) of Acid Generator Synthesis Example 1, thereby to obtain 3,3-dimethyl-2-oxobutyl thiacyclopentanium perfluorobutanesulfonate and 3,3-dimethyl-2-oxobutyl thiacyclopentanium perfluorooctanesulfonate, respectively.

$^1$H-NMR (dimethyl sulfoxide-d6, internal standard substance tetramethylsilane) of 3,3-dimethyl-2-oxobutyl thiacyclopentanium perfluorobutanesulfonate): δ(ppm) 1.15 (s, 9H); 2.13–2.23 (m, 4H); 3.33–3.38 (m, 2H), 3.47–3.54 (m, 2H); 4.85 (s, 2H).

$^1$H-NMR (chloroform-d, internal standard substance tetramethylsilane) of 3,3-dimethyl-2-oxobutyl thiacyclopentanium perfluorooctanesulfonate) δ(ppm) 1.25 (s, 9H); 2.24–2.32 (m, 2H); 2.49–2.56 (m, 2H); 3.56–3.69 (m, 4H); 5.05 (s. 2H).

Acid Generator Synthesis Example 4: Synthesis of Acid Generator B4

Into a four-necked flask, were charged 2.3 parts of 3,3-dimethyl-2-oxobutyl thiacyclopentanium bromide and 92 parts of acetonitrile, to which a solution obtained by dissolving 2.4 parts of silver p-toluenesulfonate in 7.2 parts of acetonitrile was added dropwise, followed by stirring at room temperature for 22 hours. The precipitated silver bromide was collected by filtration, and washed with 30 parts of acetonitrile. A mixture of the filtrate and the wash liquid was concentrated to 3.3 parts. Thirty parts of acetonitrile was added thereto, followed by stirring at room temperature for 2 hours, and the insoluble matters were collected by filtration. The filtrate was concentrated to 2.75 parts. The concentrated residue was recrystallized from a mixed solvent of ethyl acetate and tert-butylmethyl ether, thereby to obtain 0.68parts of the objective substance. This compound was found to be 3,3-dimethyl-2-oxobutyl thiacyclopentanium p-toluenesulfonate by $^1$H-NMR ("GX-270" manufactured by Nippon Denshi):

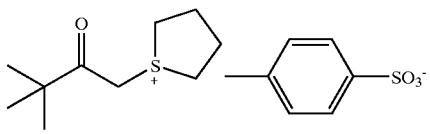

$^1$H-NMR (dimethyl sulfoxide-d6, internal standard substance tetramethylsilane): δ(ppm) 1.12 (s, 9H); 2.05–2.29 (m, 4H); 2.29 (s, 3H); 3.32–3.56 (m, 4H); 4.89 (s, 2H); 7.12 (d, 2H); 7.48 (d,2H).

Acid Generator Synthesis Example 5: Synthesis of Acid Generator B5

Into a four-necked flask, were charged 2.3 parts of 3,3-dimethyl-2-oxobutyl thiacyclopentanium bromide and 92 parts of acetonitrile, to which a solution obtained by dissolving 2.9 parts of silver camphorsulfonate in 8.8 parts of acetonitrile was added dropwise, followed by stirring at room temperature for 18 hours. The precipitated silver bromide was collected by filtration, and washed with 30 parts of acetonitrile. A mixture of the filtrate and the wash liquid was concentrated to 3.2 parts. Ten parts of acetonitrile was added thereto, followed by stirring at room temperature for 2 hours, and the insoluble matters were collected by filtration. The filtrate was concentrated to 2.92 parts. The concentrated residue was recrystallized from a mixed solvent of ethyl acetate and tert-butylmethyl ether, thereby to obtain 2.46 parts of the objective substance. This compound was found to be 3,3-dimethyl-2-oxobutyl thiacyclopentanium camphorsulfonate by $^1$H-NMR ("GX-270" manufactured by Nippon Denshi):

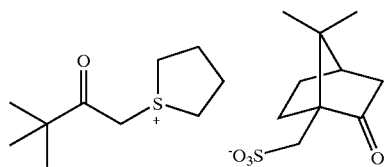

$^1$H-NMR (dimethyl sulfoxide-d6, internal standard substance tetramethylsilane): δ(ppm) 0.74 (s, 3H); 1.05 (s, 3H): 1.15 (s, 9H); 1.20–1.39 (m, 2H); 1.76–1.95 (m, 3H); 2.10–2.28 (m, 5H); 2.36 (d, 1H); 2.66–2.74 (m, 1H); 2.86 (d, 1H);3.33–3.58 (m, 4H); 4.90 (s,2H).

Resin Synthesis Example 1 (Resin A1)

2-ethyl-2-adamantyl methacrylate, 3-hydroxy-1-adamantyl methacrylate and α-methacryloyloxy-γ-butyrolactone were charged at a molar ratio of 5:2.5:2.5 (20.0 parts: 9.5 parts: 7.3 parts). Thereto, methylisobutyl ketone, the amount thereof being two times by weight based on the whole monomers, was added to form a monomer solution. Then, was added azobisisobutyronitrile as an initiator in an amount of 2 mol % based on the whole monomer. Then, the mixture was heated at 80° C. for about 8 hours. After cooling the reaction mass, it was poured into a large amount of heptane to cause precipitation. This precipitation operation was repeated three times to purify the resin. A copolymer having a molecular weight of about 9,200 was obtained. This is called Resin A1.

Resin Synthesis Example 2 (Resin A2)

2-ethyl-2-adamantyl methacrylate, 3-hydroxy-1-adamantyl acrylate, norbornene and maleic anhydride were charged at a molar ratio of 2:2:3:3 (10.0 parts: 9.0 parts: 5.7 parts: 5.9 parts). Thereto, methylisobutyl ketone, the amount thereof being two times by weight based on the whole monomers, was added to form a monomer solution, and the resulting mixture was heated up to 80° C. under nitrogen atmosphere. Then, was added azobisisobutyronitrile as an initiator in an amount of 3 mol % based on the whole monomer. Under nitrogen atmosphere, and the resulting mixture was heated at 80° C. for about 15 hours. Thereafter, the reaction mass was poured into a large amount of methanol to cause precipitation. This precipitation operation was repeated three times to purify the resin. A copolymer having a molecular weight of about 12160 and a molecular weight dispersion of 1.90 was obtained (17.1 parts). This is called Resin A2.

Resin Synthesis Example 3 (Resin A3)

2-ethyl-2-adamantyl methacrylate, 5-methacryloyloxy-2,6-norbornanelactone and α-methacryloyloxy-γ-butyrolactone were charged at a molar ratio of 2:1:1 (11.1 g:5.0 g:3.8 g), and 50 g of 1,4-dioxane was added to this to give a solution. Thereto was added 0.30 g of azobisisobutyronitrile as an initiator, then, the mixture was heated up to 85° C. and stirred for 5 hours. Then, the reaction mass was poured into a large amount of n-heptane to cause precipitation. This precipitation operation was repeated three times to purify the resin, obtaining a copolymer having a molecular weight of about 9100 and a molecular weight dispersion of 1.72. This is called Resin A3.

Resin Synthesis Example 4 (Resin A4)

Into a four-necked flask, were charged 10.5 g (42 mmol) of acrylic acid 1-(1-adamantyl)-1-methylethyl, 9.4 g (42 mmol) of acrylic acid 3-hydroxy-1-adamantyl, 6.0 g (63 mmol) of 2-norbornene, and 6.2 g (63 mmol) of maleic acid anhydride, and the mixture was dissolved in 64.2 g of methylisobutyl ketone. Nitrogen was blown therein for bubbling for 30 minutes, and then the temperature was raised up to 80° C. Into the solution was added dropwise a solution obtained by dissolving 1.0 g (6.3 mmol) of 2,2'-azobis(isobutyronitrile) in 16.0 g of methylisobutyl ketone, and the temperature was kept at 80° C. for 15 hours. The resulting reaction mass was cooled, and charged in 1134 g of methanol. As a result, a white crystal was precipitated, and the crystal was collected by filtration. The crystal was washed with methanol, and dried under reduced pressure at 30° C. for 15 hours. The crystal of copolymer of acrylic acid 1-adamantyl-1-methylethyl, acrylic acid 3-hydroxy-1-adamantyl, 2-norbornene, and maleic acid anhydride thus obtained was present in an amount of 16.4 g, and had a molecular weight of 6900 in terms of polystyrene. This is referred to as resin A4.

Resin Synthesis Example 5 (Resin A5)

(1) Into a flask, were charged 16.4 g (0.07 mol) of methacrylic acid-2-methyl-2-adamantyl, 45.4 g (0.28 mol) of p-acetoxystyrene, and 123.6 g of isopropanol. After nitrogen replacement, the temperature was raised up to 75° C. Into the solution, was added dropwise a solution obtained by dissolving 4.84 g (0.021 mol) of dimethyl 2,2-azobis(2-methylpropionate) in 9.7 g of isopropanol. The solution was aged at 75° C. for about 0.5 hour, and under reflux for about 11 hours, and then diluted with acetone. The resulting solution was charged in heptane to effect crystallization, and the crystal was collected by filtration. The crystal obtained was dried. The crystal of copolymer of methacrylic acid-2- methyl-2-adamantyl and p-acetoxystyrene obtained was present in an amount of 54.2 g.

(2) Into a flask, were charged 53.0 g (0.30 mol in terms of monomer unit) of the copolymer of methacrylic acid-2-methyl-2-adamantyl and p-acetoxystyrene (20:80) obtained above, 5.3 g (0.043 mol) of 4-dimethylaminopyridine, and 159.0 g of methanol, followed by aging under reflux for 20 hours. After cooling, the mixture was neutralized with 3.13 g (0.052 mol) of a glacial acetic acid, and the mixture was charged in water to effect crystallization. Then, the crystal was collected by filtration. Thereafter, the crystal was dissolved in acetone, and the solution was charged in water to effect crystallization. Then, the crystal was collected by filtration. A series of the operations were repeated three times, and then the crystal obtained was dried. The crystal of the copolymer of methacrylic acid-2-methyl-2-adamantyl and p-hydroxystyrene obtained was present in an amount of 37.8 g. It had a weight-average molecular weight of about 7900, and a molecular weight dispersion of 1.72 (GPC method: in terms of polystyrene). The copolymerization ratio was determined to be about 20:80 by a nuclear magnetic resonance ($^{13}$C-NMR) spectrometer. This resin is referred to as resin A5.

Resin A6: 4-hydroxystyrene/styrene/acrylic acid t-butyl (60/20/20) copolymer. weight-average molecular weight: 11000 (TSM4, manufactured by Maruzen Oil, Co., Ltd.)

Resist compositions were prepared using the acid generators B1 to B3, C1 and C2, and evaluations of the resist compositions were conducted.

Acid Generators

Acid generator B1: 3,3-dimethyl-2-oxobutyl thiacyclopentanium trifluoromethane sulfonate, Acid generator B2: 3,3-dimethyl-2-oxobutyl thiacyclopentanium perfluorobutane sulfonate Acid generator B3: 3,3-dimethyl-2-oxobutyl thiacyclopentanium perfluorooctane sulfonate Acid generator B4: 3,3-dimethyl-2-oxobutyl thiacyclopentanium p-toluene sulfonate Acid generator B5: 3,3-dimethyl-2-oxobutyl thiacyclopentanium camphor sulfonate Acid generator C1: 4-methylphenyldiphenylsulfonium perfluorooctanesulfonate, Acid generator C2: di(4-tert-butylphenyl) iodonium camphor sulfonate.

EXAMPLES 1–6 AND COMPARATIVE EXAMPLES 1–4

Resin shown in Table 1, acid generators shown in Table 1 and the components listed below were mixed and dissolved. The resultant solution was filtered through a fluorine resin filter having a pore diameter of 0.2 μm to give a resist solution.

Resin (Kind thereof is shown in Table 1) 10 parts
Acid Generator
  (Amount and kind thereof are shown in Table 1):
  Quencher: 2,6-diisopropylaniline
  (Amount thereof is listed in Table 1):
    Solvent: propyleneglycol monomethylether acetate 57 parts
    γ-butyrolactone 3 parts A silicon wafer was coated with a composition "DUV-30J" (manufactured by Brewer Co. Ltd.) and baked under conditions of 215° C. for 60 seconds so that an organic reflection-preventing membrane having a thickness of 1,600 angstrom was formed on the wafer. On the silicon wafer thus prepared, the resist solution obtained above was applied by spin-coator so that the film thickness after drying was 0.335 μm. After applying the resist solution, the wafer was pre-baked on a direct hotplate at a temperature shown in Table 1, column "PB", for 60 seconds.

The wafer having a resist film formed thereon was irradiated with an ArF eximer stepper ["NSR-ArF", manufactured by Nikon, NA=0.55, σ=0.6] through aline-and-space pattern, changing the exposure amount stepwise. The exposed wafer was subjected to post-exposure baking (PEB) on a hot plate at a temperature shown in Table 1, column "PEB", for 60 seconds. Then the wafer was subjected to paddle development with 2.38% by weight aqueous tetramethyl ammonium hydroxide solution for 60 seconds.

The developed pattern formed on a substrate was observed by a scanning electron microscope and assessed for the effective sensitivity and the resolution by the following methods:

Effective sensitivity: This is expressed in the minimum amount of exposure which gave 1:1 line-and-space pattern of 0.18 μm.

Resolution: This is expressed in the minimum size which gave line-and-space pattern spitted at the exposure amount of the effective sensitivity.

Line edge roughness (Smoothness of pattern wall): Wall of the spitted line pattern was observed by a scanning electron microscope.

Ω: The smoothness of the wall is better than those in Comparative examples.

×: The smoothness of the wall is almost same as those in Comparative examples.

Percent transmission: On a quartz glass wafer, the resist solution obtained above was applied so that the film thickness after prebaking was 0.335 μm. Then, the wafer was pre-baked according to the same conditions as above to form a resist film. Percent transmission of the resist film at 193 nm was measured by a spectrophotometer. The results are shown in Table 2.

TABLE 1

| No. | Resin | Acid generator (part) | Quencher (part) | PB (° C.) | PEB (° C.) |
|---|---|---|---|---|---|
| Example 1 | A1 | B1 (0.5) + C1 (0.2) | 0.015 | 110 | 115 |
| Example 2 | A1 | B2 (0.5) + C1 (0.2) | 0.015 | 110 | 115 |
| Example 3 | A1 | B3 (0.5) + C1 (0.2) | 0.015 | 110 | 125 |
| Example 4 | A2 | B3 (0.5) + C1 (0.2) | 0.015 | 110 | 125 |
| Example 5 | A3 | B3 (0.5) + C1 (0.2) | 0.015 | 100 | 125 |
| Example 6 | A4 | B1 (0.25) + C1 (0.2) | 0.008 | 110 | 125 |
| Comparative Example 1 | A1 | C1 (0.2) | 0.015 | 110 | 125 |
| Comparative Example 2 | A2 | C1 (0.2) | 0.015 | 110 | 125 |
| Comparative Example 3 | A3 | C1 (0.2) | 0.015 | 100 | 125 |
| Comparative Example 4 | A4 | C1 (0.2) | 0.015 | 100 | 125 |

TABLE 2

| No. | Effective sensitivity mJ/cm² | Resolution μm | Percent transmission | Line edge roughness |
|---|---|---|---|---|
| Example 1 | 48 | 0.16 | 68 | ○ |
| Example 2 | 57 | 0.15 | 68 | ○ |
| Example 3 | 41 | 0.16 | 67 | ○ |
| Example 4 | 41 | 0.16 | 67 | ○ |
| Example 5 | 70 | 0.16 | 68 | ○ |
| Example 6 | 29 | 0.16 | 65 | ○ |
| Comparative Example 1 | 53 | 0.15 | 64 | — |
| Comparative Example 2 | 76 | 0.16 | 64 | — |
| Comparative Example 3 | 88 | 0.16 | 65 | — |
| Comparative Example 4 | 44 | 0.16 | 67 | — |

As shown in Table 2, the resist compositions of Examples are better in line edge roughness (smoothness of pattern wall) than those of Comparative example. They impart good sensitivity and resolution without lowering Percent transmission.

EXAMPLES 7–12 AND COMPARATIVE EXAMPLES 5 AND 6

Resin shown in Table 3, acid generators shown in Table 3 and the components listed below were mixed and dissolved. The resultant solution was filtered through a fluorine resin filter having a pore diameter of 0.2 μm to give a resist solution.

Resin (Kind thereof is shown in Table 3) 13.5 parts
Acid Generator
(Amount and kind thereof are shown in Table 3):
Quencher: triisopropanolamine 0.07 part
Solvent: ethyllactate 60 parts A silicon wafer was coated with a composition "DUV-30J" (manufactured by Brewer Co. Ltd.) and baked under conditions of 215° C. for 60 seconds so that an organic reflection-preventing membrane having a thickness shown in Table 3 was formed on the wafer. On the silicon wafer thus prepared, the resist solution obtained above was applied by spin-coator so that the film thickness after drying was 0.49 μm. After applying the resist solution, the wafer was pre-baked on a direct hotplate at a temperature shown in Table 3, column "PB", for 60 seconds.

The wafer having a resist film formed thereon was irradiated with an KrF eximer stepper ["NSR-2205EX12B", manufactured by Nikon, NA=0.55, 2/3 annular illumination] through a line-and-space pattern, changing the exposure amount stepwise. The exposed wafer was subjected to post-exposure baking (PEB) on a hot plate at a temperature shown in Table 3, column "PEB", for 60 seconds. Then the wafer was subjected to paddle development with 2.38% by weight aqueous tetramethyl ammonium hydroxide solution for 60 seconds.

The developed pattern formed on a substrate was observed by a scanning electron microscope and assessed for the effective sensitivity and the resolution by the following methods:

Effective sensitivity; This is expressed in the minimum amount of exposure which gave 1:1 line-and-space pattern of 0.20 μm.

Resolution: This is expressed in the minimum size which gave line-and-space pattern spitted at the exposure amount of the effective sensitivity.

Line edge roughness (Smoothness of pattern wall): Wall of the spitted line pattern was observed by a scanning electron microscope.

○: The smoothness of the wall is better than those in Comparative examples.

x: The smoothness of the wall is almost same as those in Comparative examples.

Percent transmission: On a quartz glass wafer, the resist solution obtained above was applied so that the film thickness after prebaking was 0.49 μm. Then, the wafer was pre-baked according to the same conditions as above to form a resist film. Percent transmission of the resist film at 248 nm was measured by a spectrophotometer. The results are shown In Table 4.

TABLE 3

| No. | ** Å | Resin | Acid generator (part) | PB (° C.) | PEB (° C.) |
|---|---|---|---|---|---|
| Example 7 | 1600 | A5 | B2 (0.35) + C2 (0.7) | 120 | 140 |
| Example 8 | 1600 | A6 | B1 (0.35) + C2 (0.35) | 130 | 140 |
| Example 9 | 1600 | A6 | B2 (0.35) + C2 (0.35) | 130 | 140 |
| Example 10 | 1600 | A6 | B3 (0.35) + C2 (0.35) | 130 | 140 |
| Example 11 | 600 | A6 | B4 (0.35) + C2 (0.35) | 130 | 140 |
| Example 12 | 600 | A6 | B5 (0.35) + C2 (0.35) | 130 | 140 |
| Comparative Example 5 | 1600 | A5 | C2 (0.7) | 120 | 140 |
| Comparative Example 6 | 1600 | A6 | C2 (0.35) | 130 | 140 |

**Thickness of reflection-preventing membrane

TABLE 4

| No. | Effective sensitivity mJ/cm² | Resolution μm | Percent transmission | Line edge roughness |
|---|---|---|---|---|
| Example 7 | 50 | 0.16 | 72 | ○ |
| Example 8 | 78 | 0.16 | 76 | ○ |
| Example 9 | 82 | 0.16 | 76 | ○ |
| Example 10 | 90 | 0.16 | 76 | ○ |
| Example 11 | 82 | 0.16 | 75 | ○ |
| Example 12 | 96 | 0.16 | 75 | ○ |
| Comparative Example 5 | 48 | 0.16 | 72 | — |
| Comparative Example 6 | 120 | 0.19 | 77 | — |

As shown in Table 4, the resist compositions of Examples are better in line edge roughness (smoothness of pattern wall) than those of Comparative example. They impart good sensitivity and resolution without lowering Percent transmission.

The chemical amplifying type positive resist composition of the present invention provides a resist pattern having an exceedingly improved line edge roughness, and it is also excellent in various resist performances such as dry etching resistance, sensitivity, and resolution. Therefore, this composition is suitable for lithography using a KrF excimer laser, or an ArF excimer laser, whereby a high-performance resist pattern can be provided.

What is claimed is:

1. A chemical amplifying type positive resist composition which comprises:
   (A) an acid generator containing (a) a sulfonium salt represented by the following formula (I):

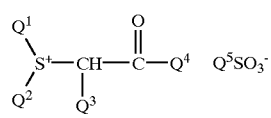

(I)

wherein $Q^1$ and $Q^2$ each independently represent a straight chain or branched alkyl group having from 1 to 6 carbon atoms or a cycloalkyl group having from 3 to 10 carbon atoms, or $Q^1$ and $Q^2$ form, together with a sulfur atom to which $Q^1$ and $Q^2$ are adjacent, a heteroalicyclic group which may further contain an oxygen atom and a sulfur atom; $Q^3$ represents a hydrogen atom, $Q^4$ represents a straight chain or branched alkyl group having from 1 to 6 carbon atoms or a cycloalkyl group having from 3 to 10 carbon atoms, or $Q^3$ and Q4 form, together with a CHC(O) group to which $Q^3$ and Q4 are adjacent, a 2-oxocycloalkyl group; and $Q^5SO_3^-$ represents an organosulfonate ion, provided that when $Q^5$ represents a perfluoroalkyl group having from 1 to 8 carbon atoms, there is excluded the case where $Q^1$ represents a straight chain or branched alkyl group having from 1 to 6 carbon atoms, $Q^2$ represents a straight chain or branched alkyl group having from 1 to 6 carbon atoms, or a cycloalkyl group having from 3 to 10 carbon atoms, and $Q^3$ and $Q^4$ represent, together with their adjacent CHC(O) group, a 2-oxocycloalkyl group, and (b) at least one onium salt selected from a triphenylsulfonium salt represented by the following formula (IIa), and a diphenyliodonium salt represented by the following formula (IIb):

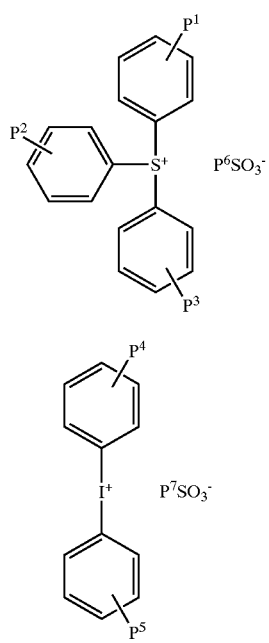

wherein $P^1$ to $P^5$ each independently represent hydrogen, a hydroxyl group, an alkyl group having from 1 to 6 carbon atoms, or an alkoxy group having from 1 to 6 carbon atoms; and $P^6SO_3^-$ and $P^7SO_3^-$ each independently represent an organosulfonate ion; and (B) a resin which has a polymerization unit having a group unstable against an acid, and is alkali-insoluble or -slightly soluble itself, but is converted to alkali-soluble by the action of an acid.

2. The chemical amplifying type positive resist composition according to claim 1 wherein $Q^1$ and $Q^2$ form, together with a sulfur atom to which $Q^1$ and $Q^2$ are adjacent, a heteroalicyclic group.

3. The chemical amplifying type positive resist composition according to claim 1 wherein $Q^5$, $P^6$ and $P^7$ each independently are a perfluoroalkyl group having from 1 to 8 carbon atoms, an alkyl group having from 1 to 8 carbon atoms, an aromatic group having from 6 to 12 carbon atoms or a camphor group.

4. The chemical amplifying type positive resist composition according to claim 1 wherein the amounts ratio of the sulfonium salt represented by the formula (I) to the onium salt selected from the triphenylsulfonium salt represented by the formula (IIa) and diphenyliodonium salt represented by the formula (IIb) is in the range of about 9:1 to 1:9 by weight.

5. The chemical amplifying type positive resist composition according to claim 1 wherein (B) the resin contains the polymerization unit having a group unstable against an acid in an amount in the range of from 10 to 80 mol %.

6. The chemical amplifying type positive resist composition according to claim 1 wherein the polymerization units having a group unstable against an acid is a polymerization unit of (meth)acrylic acid 2-alkyl-2-adamantyl or (meth) acrylic acid 1-adamantyl-1-alkylalkyl.

7. The chemical amplifying type positive resist composition according to claim 1 wherein (B) the resin further contains at least one polymerization unit selected from a polymerization unit of p-hydroxystyrene; a polymerization unit of m-hydroxystyrene; a polymerization unit of (meth) acrylic acid 3-hydroxy-1-adamantyl; a polymerization unit of (meth)acrylic acid 3,5-hydroxy-1-adamantyl; a polymerization unit of (meth)acryloyloxy-γ-butyrolactone in which the lactone ring may be substituted by alkyl; polymerization units of alicyclic lactones each represented by the following formulae (IIIa) and (IIIb);

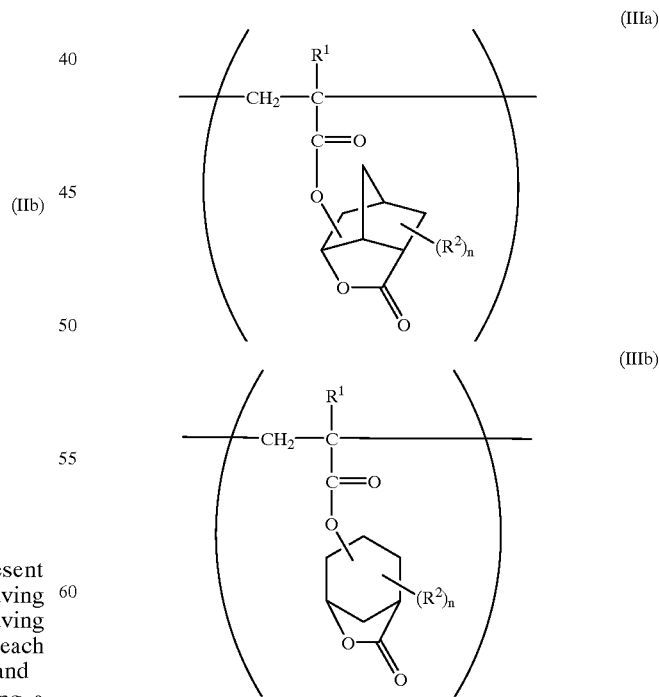

wherein $R^1$ and $R^2$ each independently represent hydrogen or methyl, and n represents a number of from 1 to 3.

8. The chemical amplifying type positive resist composition according to claim 7 wherein (B) the resin further contains a polymerization unit of 2-norbornene and a polymerization unit of an aliphatic unsaturated dicarboxylic acid anhydride.

9. The chemical amplifying type positive resist composition according to claim 1 which further comprises an amine as quencher.

* * * * *